US010527470B1

(12) United States Patent
Hassan et al.

(10) Patent No.: US 10,527,470 B1
(45) Date of Patent: Jan. 7, 2020

(54) METERING SYSTEM FOR THREE-PHASE OIL FLOW IN HORIZONTAL PIPELINE

(71) Applicant: King Fahd University of Petroleum and Minerals, Dhahran (SA)

(72) Inventors: Essam E. M. Hassan, Dhahran (SA); Sharif I. M. Sheikh, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 16/216,196

(22) Filed: Dec. 11, 2018

(51) Int. Cl.
*G01F 1/56* (2006.01)
*G01F 15/06* (2006.01)
(Continued)

(52) U.S. Cl.
CPC .............. *G01F 1/56* (2013.01); *G01F 1/74* (2013.01); *G01F 15/063* (2013.01); *G01N 33/2823* (2013.01)

(58) Field of Classification Search
CPC ................... G01F 1/56; G01F 1/74; G01F 15/063; G01N 33/2823; G01N 24/082
See application file for complete search history.

(56) References Cited

U.S. PATENT DOCUMENTS

| 6,255,817 B1 * | 7/2001 | Poitzsch | G01N 24/081 324/303 |
| 6,984,980 B2 | 1/2006 | Kruspe et al. | |

(Continued)

FOREIGN PATENT DOCUMENTS

| EP | 2 416 127 B1 | 3/2015 |
| JP | 3150985 | 1/2001 |
| KR | 10-2016-0068538 | 6/2016 |

OTHER PUBLICATIONS

Wu, et al. ; Design of a Conductance and Capacitance Combination Sensor for water holdup measurement in oil-water two-phase flow ; ScienceDirect ; Flow Measurement and Instrumentation vol. 46 Part B ; pp. 218-229 ; Dec. 2015 ; Abstract ; 3 Pages.

(Continued)

*Primary Examiner* — Peter J Macchiarolo
*Assistant Examiner* — John M Royston
(74) *Attorney, Agent, or Firm* — Oblon, McClelland, Maier & Neustadt, L.L.P.

(57) ABSTRACT

An apparatus, method and non-transitory computer readable medium method are described for identifying the phase fractions and flow-rate of a petroleum carrying pipeline with three-phase wavy-stratified flow. A set of semi-cylindrical electrodes are mounted on the internal surface of a pipe to monitor the total capacitance and resistance of the three-phase contents. The phase fractions are determined by relating the resistance and capacitance to the phase-angles associated with the interfaces between water, oil and gas phases of the mixture. To calculate the flow rate, measured capacitances from two sets of electrodes with known separation distance are cross-correlated to determine time delay. Communications circuitry transmits the measurements to a remote control center for monitoring. Calculated and measured results demonstrate close agreement. The percentage error exhibited by the proposed inclined capacitive plate technique is calculated and compared with published values.

17 Claims, 19 Drawing Sheets

A Cross section of the pipe with the three-phase Gas-Oil-Brine

(51) Int. Cl.
*G01F 1/74* (2006.01)
*G01N 33/28* (2006.01)

(56) References Cited

U.S. PATENT DOCUMENTS

2002/0139197 A1* 10/2002 Salamitou ................ G01F 1/44
73/861.04
2015/0033823 A1 2/2015 Blumberg, Jr.

OTHER PUBLICATIONS

Das, et al. ; A Semi-Cylindrical Capacitive Sensor Used for Soil Moisture Measurement ; World Academy of Science, Engineering and Technology ; International Journal of Electronics and Communication Engineering vol. 8, No. 1 ; 2014 ; 6 Pages.
Iqbal ; Novel Metering System for the Three Phase Flow in Horizontal Oil Pipes Under Steady Flow ; Thesis ; 2015 ; 144 Pages.
Sheikh, et al. ; Capacitance Based Monitoring of a Crude-Oil Flow using Internal/External Electrodes ; EE Department ; King Fand University of Petroleum and Minerals ; 5 Pages.
Cisco Validated Design ; Operational Telecom Network for the Connected Pipeline System Design Guide ; Jul. 12, 2016 ; 58 Pages.
Types of Oil & Gas Pipeline ; https://blog.miragemachines.com/types-of-pipeline-every-oil-and-gas-engineer-should-know-about ; 3 Pages.
U.S. Department of Transportation ; Petroleum Pipeline Systems ; Pipeline & Hazardous Materials Safety Administration ; 2 Pages.

* cited by examiner

A Cross section of the pipe with the three-phase Gas-Oil-Brine

METERING SYSTEM FOR THREE-PHASE OIL FLOW IN HORIZONTAL PIPELINE

BACKGROUND

Technical Field

The present disclosure relates to a non-invasive electrode arrangement and method for using the non-invasive electrode arrangement. The electrode arrangement can be placed on the internal surface of a horizontal pipeline to accurately measure the stratified three-phase (oil, water, gas) volumes within the pipeline and the velocity of the pipeline contents at the measuring location.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Petroleum transportation often results in a three-phase laminar or steady-state flow of liquids, where gas, oil and water flows with minimal mixing between the phases. The volume estimation of oil-gas-brine, known in the oil industry by the term three-phase flow which is the simultaneous flow of the three substances in horizontal pipelines, poses a challenging problem for engineers. Several techniques have been developed to estimate the contents of each phase and the flow rate. These techniques are either mechanical, electrical or combined in nature.

Mechanical techniques include methods which use any of turbo meter sampling tubes, vortex meters and vibrating densitometers. The drawback of these techniques is that they depend on measurement of temperature and pressure within the pipe and require complicated methods of integrating the measurement devices and their sensed signals.

Non-invasive electrical measurements are known for making such measurements. A capacitive measurement method using multiple copper-electrodes which requires an integrated microcontroller to monitor two-phase flow was reported by Libert et al., "Capacitive measuring system for two-phase flow monitoring", Part 1: hardware design and evaluation", Flow Measurement and Instrumentation, vol. 47, pp. 90-99, 2016, incorporated herein by reference in its entirety. A correlative flow meter which employs the conductance of the mixture and the water content to determine the measurements was described by Xue and Shen. See G. Xue and Y. Shen, "Study on the measurement of oil gas water three-phase flow with conductance correlative flow meter," Proceedings of IEEE, International Conference on Automation and Logistics, Qingado, China, September 2008, pp. 1295-1297, incorporated herein by reference in its entirety.

As an example of a non-invasive measurement, microwave measurements have been employed by placing crossed dipole antenna pairs at different locations inside the pipe, exciting a single antenna pair and recording the response at the other antenna pairs. By correlating the results, the unknown volumes were able to be estimated. See: Isaksen, "Three Phase Pipe Flow Imaging Using a Capacitance Tomography System," IEEE Colloquium on Advances in Sensors for Fluid Flow Measurements, 1996, pp 11/1-11/6; Z. Qu, Q. Zhao and Y. Meng, "On oil measurement of water concentration of oil-water mixture in the flow of pipe line by using eddy current," Journal of Measurement Science and Technology, Vol. 4, No. 1, October 2012; L. Al-Hadhrami, S. Shaahid, L. Tund and A. Al-Sarkhi, "Experimental study on the flow regimes and pressure gradients of air-oil-water three phase flow in horizontal pipes," Scientific World, Vol. 2014, Article ID 810527; Sheikh S. I., Al-Quraish K., Ragheb H. A and Babelli I. "Simple Microwave Method for Detecting Water Holdup", Microwave and Optical Technology Letters, Vol. 50, No. 2, pp. 354-355, February 2008; J. Hitomi, Y. Murai, H. J. Park and Y. Tasaka, "Ultra sound flow monitoring and flow metering of air-oil-water three layers pipe flows," IEEE Access, Vol. 5, pp 15021-15029, 2017, each incorporated herein by reference in its entirety.

Capacitative sensor plates have been used to measure soil moisture using an alternating current technique, (See "A Semi-Cylindrical Capacitive Sensor Used for Soil Moisture Measurement", S. Das, T. Sarkar, B. Chakraborty, International Science Index, Electronics and Communication Engineering, Vol. 8, No. 1, 2014), incorporated herein by reference in its entirety. However, the work of Das does not measure velocity or relative levels of layers of soil and water, and uses a different method of analysis than the present disclosure.

In a pipeline system, communications with a control center are important in order to ensure pipeline safety and operability. Field devices are the instrumentation and data gathering units, such as the volume and flow measurement device of the present disclosure, and communication systems. Field devices are installed along the pipeline at specific locations, such as injection or delivery stations, pump stations (liquid pipelines) or compressor stations (gas pipelines), and block valve stations.

The information measured by these field instruments is then gathered in local remote terminal units (RTU) that transfer the field data to a central location in real time using communication systems, such as satellite channels, microwave links, or cellular phone connections.

Pipelines are controlled and operated remotely, from a control center. In this control center, all the data related to field measurement is consolidated in one central database. The data is received from multiple RTUs along the pipeline. It is common to find RTUs installed at every station along the pipeline.

Supervisory control and data acquisition (SCADA) is a system of software and hardware elements that allows pipeline control centers to control processes locally or at remote locations and monitor, gather, and process real-time data.

A SCADA system at a pipeline control center receives all the field data and monitors pressure, flow and temperature amongst other operating data that is communicated back to servers and applications in the control center. This data is then displayed to operators where near real time decisions can be made for safe transport of the product along the pipeline.

The pipeline requires connectivity for communications between control centers, between the control centers and the pipeline stations, and for any inter-station communication along the pipeline. A communications network can include using various connectivity options (such as Ethernet, Multiprotocol Label Switching [MPLS], dense wavelength-division multiplexing [DWDM], Optical Transport Network (OTN), cellular, wireless).

Various types of stations may run along the pipeline. (See FIG. 4-FIG. 6). A pipeline segment may be bookended with larger stations such as a main terminal or a pumping/ compressor station. In between these larger facilities may be intermediate stations, such as metering stations and block valve station. When fiber connectivity is available, deployment options typically include Ethernet, IP, MPLS, and DWDM. For areas where fiber is not available, secure wireless or cellular-based services such as Worldwide Interoperability for Microwave Access (WiMAX), Third-Generation Mobile Network (3G), Long Term Evolution (LTE), and satellite can provide connectivity for the pipeline operations. (See Cisco Design Guide, "Operational Telecom Network for the Connected Pipeline System Design Guide", Jul. 12, 2016, https://www.cisco.com/c/dam/en_us/solutions/industries/docs/manufacturing/operational-telecom-network-connected-pipeline-design-guide.pdf).

The present disclosure seeks to improve the measurements of oil, gas and brine volumes and the velocity of the mixture in a pipeline by presenting a measurement apparatus which includes a non-invasive semi-cylindrical electrode arrangement and simple mathematical calculations. The non-invasive electrode arrangement is placed on the internal/external surface of a pipe segment in a near-horizontal pipeline to accurately measure the capacitance and resistance of the three-phase contents of the pipe. Relating the measured values with phase angles determined from the mathematical calculations determines the volumes of gas, oil and water within the pipeline and the velocity of the pipeline contents at the measuring location. The measurements may then be transmitted to a control center for use in monitoring the pipeline flow.

SUMMARY

In an exemplary embodiment, an apparatus is described for measuring the water, oil and gas volumes within a cylindrical horizontal pipeline and the velocity of the oil flowing in the pipeline, wherein the pipeline has a circular cross-sectional area of radius (Rad), and an axial length (Z), the apparatus comprising plurality of pipe sections, wherein at least one pipe section has an internal structure including a first semi-cylindrical conducting sheet covering a portion of the internal surface of the pipe section and a second semi-cylindrical conducting sheet covering an opposing portion of the internal surface of the pipe section, wherein each semi-cylindrical sheet has radius (Rad) and axial length $z_0$, wherein the at least one pipe section is installed a first location within the pipeline, wherein a gap ($2\delta$) exists between an edge of the first semi-cylindrical conducting sheet and a corresponding edge of the second semi-cylindrical conducting sheet; a first conductive terminal installed along the central axial line of the first semi-cylindrical conducting sheet and a second conductive terminal installed at the central axial line of the second semi-cylindrical conducting sheet, wherein each conductive terminal is placed on the external surface of the pipe section and protrudes through the pipe to electrically contact a respective semi-cylindrical sheet.

The apparatus includes a control unit comprising a power supply to apply a positive DC voltage at the first terminal and a negative DC voltage at the second terminal; a switch connected between the power supply and the first terminal; a controller having circuitry configured to control the switch; measuring circuitry connected to the conductive terminals to measure the capacitance and resistance between the terminals. processing circuitry configured to determine the respective volumes of water, oil and gas in the pipe section based on the capacitance and resistance measurements by relating the phase-angles and the measured values, and to calculate the velocity of the oil flowing in the pipeline.

In another exemplary embodiment, a method includes measuring the water, oil and gas volumes within a cylindrical horizontal pipeline and the velocity of the oil flowing in the pipeline, wherein the pipeline has a circular cross-sectional area of radius (Rad), and an axial length (Z), the method comprising installing, within the pipeline having a plurality of pipe sections, at least one pipe section having an internal structure including a first semi-cylindrical conducting sheet covering a portion of the internal surface of the pipe section and a second semi-cylindrical conducting sheet covering an opposing portion of the internal surface of the section of the pipe section, wherein each semi-cylindrical sheet has radius (Rad) and axial length $z_0$ so that a gap ($2\delta$) exists between an edge of the first semi-cylindrical conducting sheet and a corresponding edge of the second semi-cylindrical conducting sheet, installing a first conductive terminal along the central axial line of the first semi-cylindrical conducting sheet and a second conductive terminal at the central axial line of the second semi-cylindrical conducting sheet so that each conductive terminal is located on the external surface of the pipe section and protrudes through the pipe section to electrically contact a respective semi-cylindrical sheet; connecting the conductive terminals to a control unit including a controller having circuitry configured for applying a positive DC voltage at the first terminal and a negative DC voltage at the second terminal and for measuring the resistance and capacitance at the conductive terminals; the control unit further having processing circuitry for determining the respective volumes of water, oil and gas in the pipe section and calculating the velocity of the oil flowing in the pipeline.

In an optional embodiment, the first and second semi-cylindrical conducting sheets may be placed on the external surface of the pipe section.

In another exemplary embodiment, a non-transitory computer readable medium is described, the non-transitory computer readable medium having instructions stored therein that, when executed by one or more processors, cause the one or more processors to perform a method for measuring the water, oil and gas volumes within a cylindrical horizontal pipe section and the velocity of the oil flowing in the pipeline, wherein the pipeline has a circular cross-sectional area of radius (Rad) and an axial length (Z), the pipeline having a plurality of pipe sections, at least one pipe section having an internal structure including a first semi-cylindrical conducting sheet covering a portion of the internal surface of the pipe section and a second semi-cylindrical conducting sheet covering an opposing portion of the internal surface of the section of the pipe section, wherein each semi-cylindrical sheet has radius (Rad) and axial length $z_0$, so that a gap ($2\delta$) exists between an edge of the first semi-cylindrical conducting sheet and a corresponding edge of the second semi-cylindrical conducting sheet, and a first conductive terminal installed along the central axial line of the first semi-cylindrical conducting sheet and a second conductive terminal installed at the central axial line of the second semi-cylindrical conducting sheet so that each conductive terminal is located on the external surface of the pipe section and protrudes through the pipe section to electrically contact a respective semi-cylindrical sheet; the method comprising: applying a positive DC voltage at the first terminal and a negative DC voltage at the second terminal, the conductive terminals connected to a control unit; measuring, by a controller in the control unit and having circuitry configured for measuring, the resistance between the first and second terminals; calculating, by the processing circuitry, the capacitance of the water layer using the measured resistance and the following equations:

$$C = \frac{\varepsilon_0 \varepsilon_r}{2\phi_0} \ln\left(\frac{b}{a}\right) F/m$$

and the relationship $$R = \frac{\varepsilon_0 \varepsilon_r}{C\sigma},$$

where R and C are the resistance and capacitance of the water layer, wherein $\varepsilon_0$=8.854 e−12, σ (s/m) is the conductivity of the element under measurement; εr is the relative dielectric constant of the phase under measurement, and "a", "b" and $\phi_0$ are measurements as shown in FIG. 1A.

The method continues by calculating the total resistance and the capacitances of the semi-cylindrical sheets based on the following equations:

$$R = \sum_1^N \left(\frac{1}{\sigma}\right) 2\phi_n / \ln(b_n/a_n) \text{ohms}/m$$

$$\text{and } C_T = \sum_{n=0}^N \left(\frac{\varepsilon_0 \varepsilon_r}{2\phi_n} \ln\left(\frac{b_n}{a_n}\right)\right) F/m$$

wherein δ is the angle subtended by a sector from the center of the pipe section to the edges of the gap; "N" is the number of pairs of chords subtended by an angle 2δ, β1 is the angle from the center of the pipe section to the top of the oil volume, β2 is the angle from the center of the pipe section to the top of the water volume, and $a_n = \rho_0 * \{\text{Cos}(\delta)\text{cot}(\beta_{2n}) - \text{Sin}(\delta)\}$ $b_n = \rho_0 * \{\text{Cos}(\delta)\text{cot}(\beta_{2n}) + \text{Sin}(\delta)\}$ $\beta_{2n} = (2n+1)\delta$ radians, with n=0, 1, 2 . . . , N, $$N = \left(\frac{90°}{2\delta}\right) - 1$$

and $\phi_n = \beta_{2n}$ radians

The method continues by defining, by the processing circuitry, the volume of water as having a height (hw) measured along the vertical radius of the cross section of the pipe section, the oil content as having a height (ho) measured along the vertical radius of the cross section of the pipe section, the gas as having a height (hg) measured along the vertical radius of the cross section of the pipe section, wherein 2Rad=hw+ho+hg, and calculating, by the processing circuitry, the respective heights of the water, oil and gas within the pipe section;

determining at a time ($\tau_0$), second capacitance and second resistance at a second pipe section having a second internal structure and located at a second location within the pipeline, the second internal structure separated by a distance (d) from the first internal structure, wherein ($\tau_0$) is the time elapsed between a capacitance measurement at the first location and a capacitance measurement at the second location, and calculating, by the processing circuitry, the velocity of the oil flowing in the pipeline based on the equation velocity=d/$\tau_0$, the capacitance and resistance measurements of the first pipe section and the second capacitance and second resistance measurements of the second pipe section; calculating, by the processing circuitry, the volume of oil flowing per unit time, based on the equation:

$$\text{Volume of } \frac{\text{oil}}{\text{time}} = (\pi * \text{Rad}^2 - V_g - V_w) * \text{velocity,}$$

$V_g = \beta 1 \times \text{Rad}^2 - \text{Rad}^2 \times \cos(\beta 1) \times \sin(\beta 1)$ $V_b = \beta 3 \times \text{Rad}^2 - \text{Rad}^2 \times \cos(\beta 3) \times \sin(\beta 3)$ wherein "Rad" is the pipe radius and Vg, and Vw and β1 and β3 are phase-angles of the gas and water regions, respectively.

The third embodiment further comprises transmitting, by communications circuitry in the control unit, the measurements of the volumes of water, oil and gas in the pipe section and the velocity of the oil flowing in the pipeline between the first and second sections to a remote control center using wired or wireless communication.

A fourth embodiment includes an experimental testing arrangement comprising Plexiglas pipeline sections, a water pump; an oil pump; a return pump and a gas supply; a control unit comprising a power supply to apply a positive DC voltage at the first terminal and a negative DC voltage at the second terminal; a switch connected between the power supply and the first terminal; a controller having circuitry configured to control the switch, water pump, oil pump and return pump; data acquisition circuitry connected to the conductive terminals to measure the capacitance and resistance between the terminals; and processing to circuitry configured determine the respective volumes of water, oil and gas in the pipe sections based on the capacitance and resistance and to calculate the velocity of the oil flowing in the pipe sections.

Error estimation of the phase fractions and the velocity in the pipeline in a dynamic measurement system is an important benchmarking tool. Several experiments using the apparatus of the fourth embodiment are conducted to determine the error rate by comparing known phase fractions with phase fractions of the pipeline contents calculated by the methods of the present disclosure.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein:

FIG. 1G illustrates an example of an LCR meter.

DETAILED DESCRIPTION

Figure 1A:
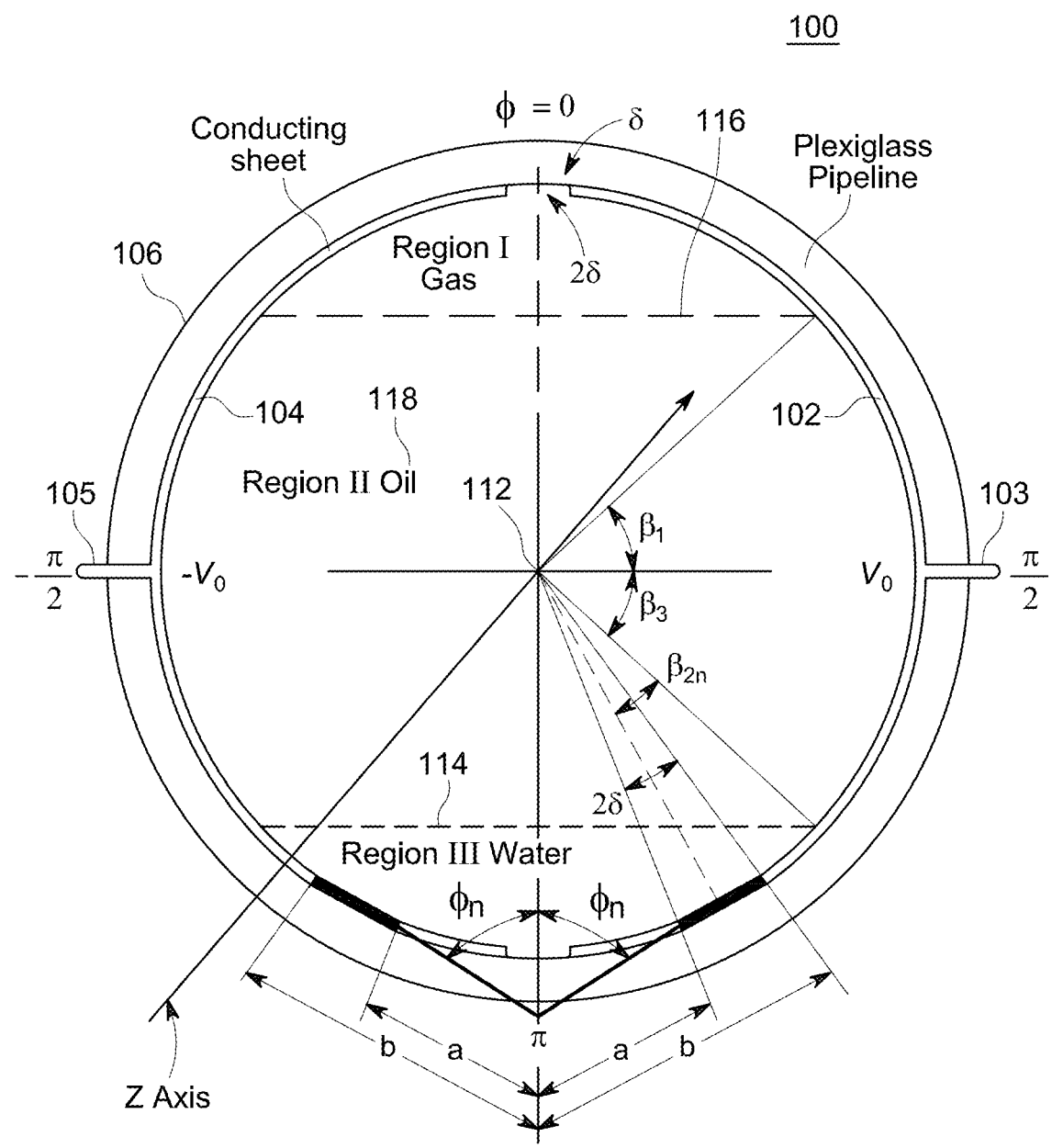
FIG. 1A depicts the cross section of the pipe section illustrating the two electrode arrangement, according to certain embodiments.

In the drawings, like reference numerals designate identical or corresponding parts throughout the several views. Further, as used herein, the words "a," "an" and the like generally carry a meaning of "one or more," unless stated otherwise. The drawings are generally drawn to scale unless specified otherwise or illustrating schematic structures or flowcharts.

Furthermore, the terms "approximately," "approximate," "about," and similar terms generally refer to ranges that include the identified value within a margin of 20%, 10%, or preferably 5%, and any values therebetween.

In a three-phase horizontal pipeline, the different densities of the oil, gas and water drive the brine layer to the bottom, oil layer to the middle and gas-layer to the top of the flow.

The water may be brine and the gas may be natural gas, ethane, butane, propane, carbon dioxide, air or mixtures of the gases. These layers have distinct separating planes for a steady state flow. Referring to FIG. 1A, the cross section of a pipe section including the two electrode arrangement is shown. The height of the brine is designated as 'hw', that of the oil "ho" and that of the gas "hg". For a pipe radius, Rad, 2×Rad=hw+ho+hg.

Aspects of the present disclosure are directed to an apparatus and methods for measuring water, oil and gas volumes within a cylindrical horizontal pipeline and the velocity of the oil flowing in the pipeline. The apparatus is non-invasive, which preserves the integrity of the pipeline.

The following aspects present a simple non-intrusive inclined capacitive plate technique to calculate the capacitance and resistance of three-phase mixture.

In some aspects, a non-intrusive inclined capacitive plate technique is used to calculate the capacitance and resistance of a three-phase wavy-stratified flow. The monitored section of the pipeline includes two semi-cylindrical electrodes mounted on the inside surface with each electrode covering nearly one half of the pipeline. To calculate the capacitance and resistance of this semi-cylindrical capacitor, a processor divides the cross-sectional area of the electrode assembly into 'N' pairs of inclined chords, where the magnitude of "N" is limited by the expected accuracy and computational resources. An oppositely polarized low-frequency signal is applied to the electrodes. Once calibrated, the measured capacitances represent the total capacitances of the gas, oil and water mixture within the pipe. The measured resistance is primarily that of the water layer, as the water layer has the lowest resistivity of the three phases. Correlating the capacitances and resistances with the phase angles associated with the phase separation plane yields the calculation of the phase fractions.

In some aspects, the pipe section is made of Plexiglas.

In another aspect, the semi-cylindrical electrodes are mounted on the external surface of the pipe.

In some aspects, an apparatus and method are described which calculate the volume of oil-gas-brine under steady state conditions by measuring both the conductance and the capacitance of the flow inside the pipe. Two electrodes, each having the form of a conducting metallic sheet, are each placed to cover one half of the internal surface of the pipe, with a gap between the sheets. The two electrodes are used to measure the conductance of the mixture of oil, gas and water/brine, which conductance is primarily due to the brine content, and to measure the compound capacitance of the three substances.

In some aspects, a method for calculating the flow velocity is based on the measurement of the values of capacitance at different locations in a correlative flow method to determine the speed of flow. The correlative flow measurement is based on measurements of the conductivity of the water in the flow. Analysis results demonstrate that the above measurements are sufficient to calculate the volume of each of the three phases in the pipe.

Figure 1B:
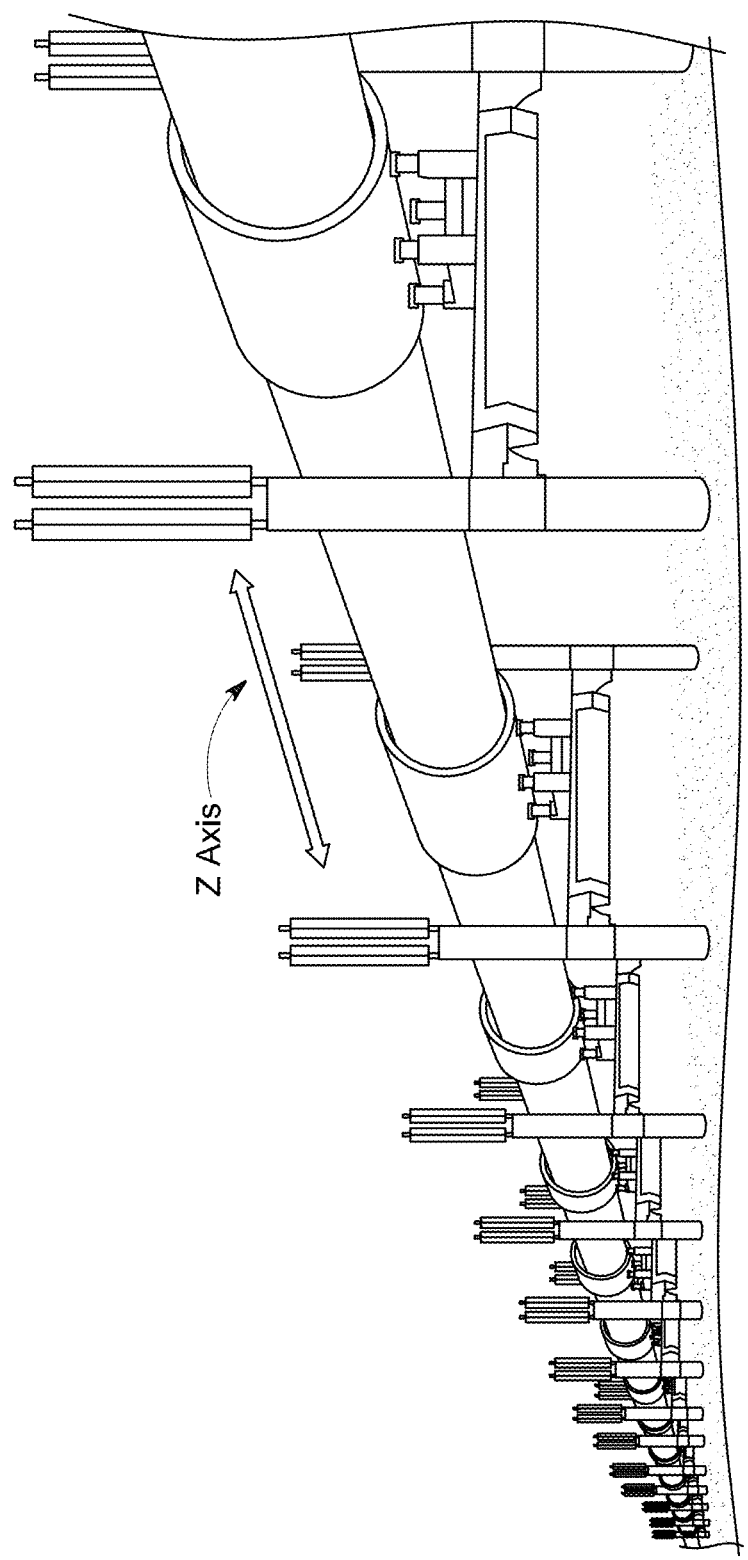
FIG. 1B depicts a pipeline, according to certain embodiments.
Figure 1C:
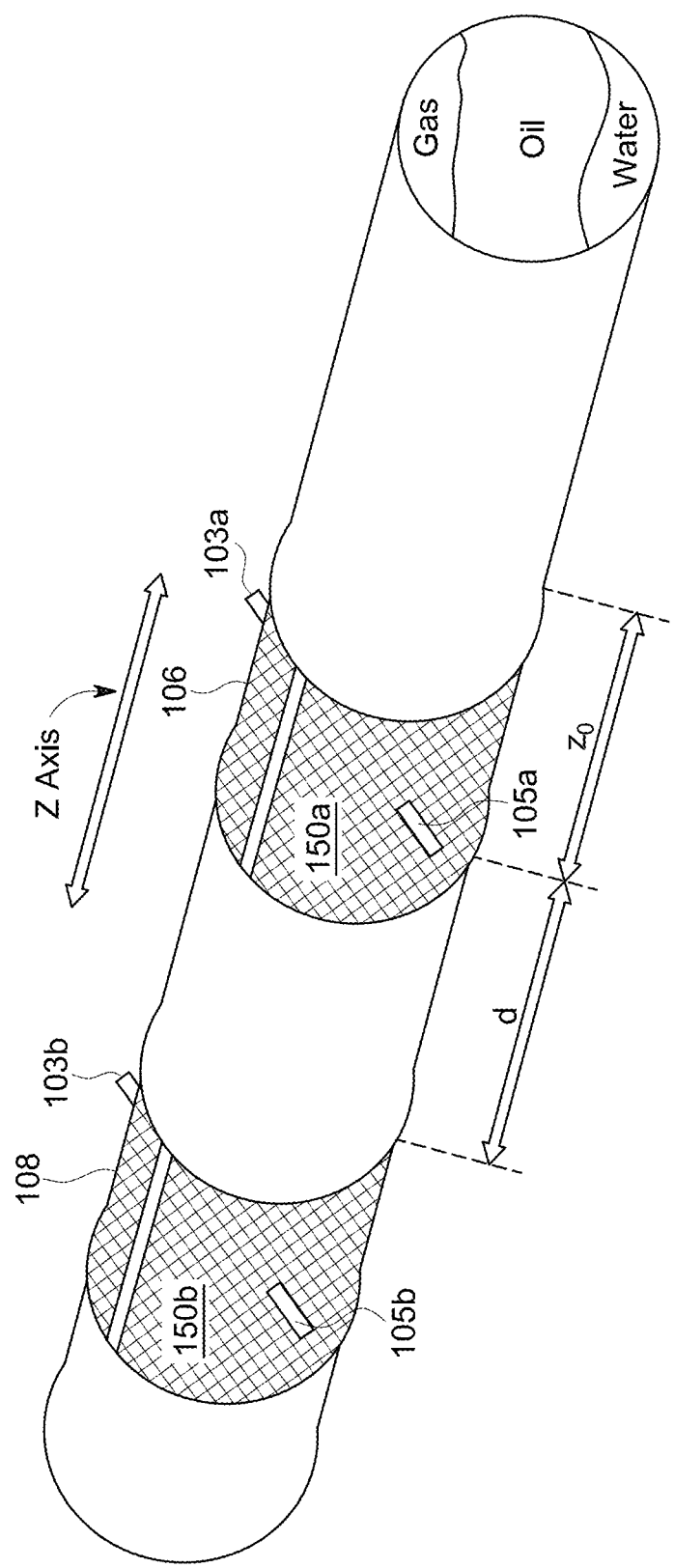
FIG. 1C depicts an exemplary pipeline, according to certain embodiments.
Figure 1D:
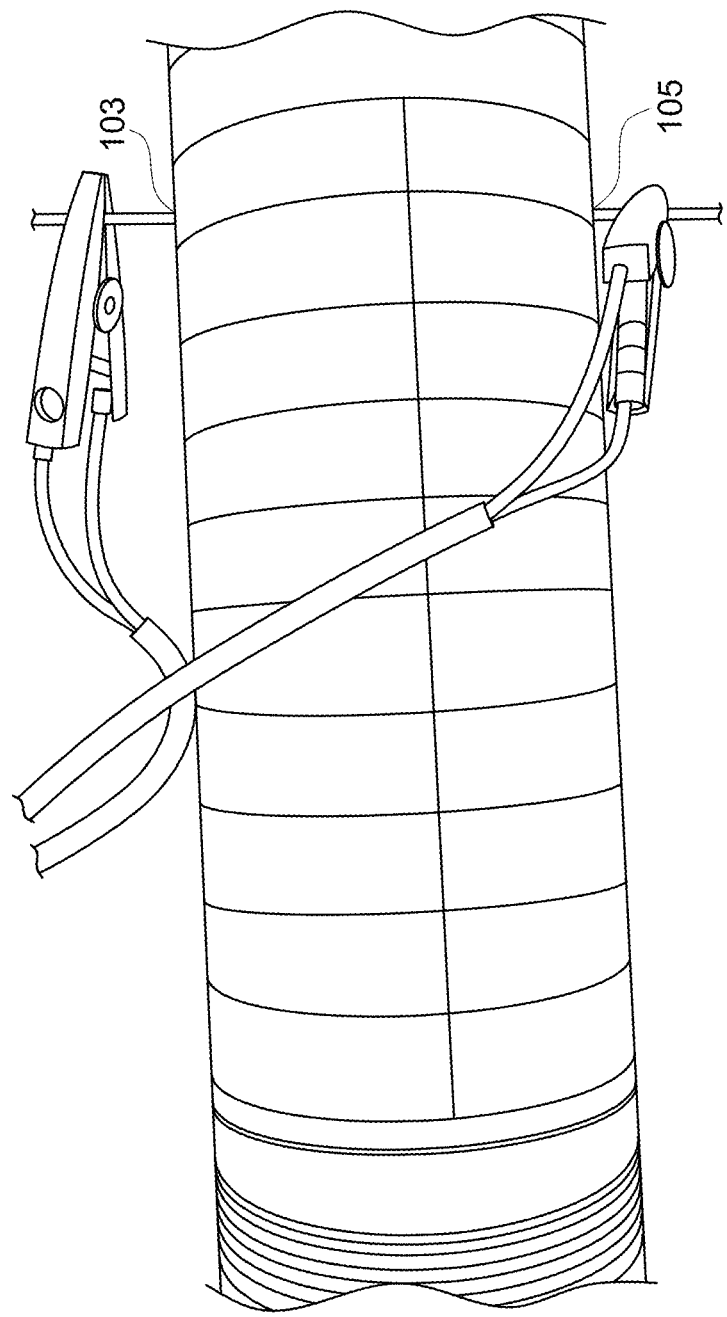
FIG. 1D depicts a pipe section including the two electrode arrangement with measuring poles, according to certain embodiments.

According to a first embodiment shown in FIG. 1A, 1C and 1D, an apparatus for measuring the water, oil and gas volumes within a cylindrical horizontal pipeline and the velocity of the oil flowing in the pipeline is described, wherein the pipeline has a circular cross-sectional area of radius (Rad), and an axial length (Z).

Referring to FIG. 1B, a non-limiting example of a pipeline is shown. See "Types of Pipeline Every Oil and Gas Engineer Should Know About", Mirage Machines Portable Performance Blog, https://blog.miragemachines.com/types-of-pipeline-every-oil-and-gas-engineer-should-know-about last accessed on Oct. 10, 2018, incorporated herein by reference.

Oil pipelines are made from stainless steel or carbon steel pipes, cast iron or wrought iron pipes, or plastic pipes, such as polyethylene (PE) pipes, polyamide-11 (PA-11) thermoplastic pipes, polyamide-12 (PA-12) thermoplastic pipes. (See "Pipeline Materials", PHMSA-Pipeline and hazardous materials safety administration, May 3, 2017, https://www.phmsa.dot.gov/technical-resources/pipeline/pipeline-materials). Pipe sections for measuring the phase fractions and the flow velocity may be made of Plexiglas.

The pipeline includes a plurality of pipe sections, shown as 106 and 108 in FIG. 1C. As shown in FIGS. 1A and 1C, at least one pipe section has an internal structure including a first semi-cylindrical conducting sheet 102 covering a portion of the internal surface of the pipe section and a second semi-cylindrical conducting sheet 104 covering an opposing portion of the internal surface of the pipe section, wherein each semi-cylindrical sheet has radius (Rad) and axial length $z_0$, wherein the at least one pipe section is installed a first location within the pipeline, wherein a gap ($2\delta$) exists between an edge of the first semi-cylindrical conducting sheet and a corresponding edge of the second semi-cylindrical conducting sheet.

The gap region is filled in with sand glue (as an insulator) so that when saline water (brine) partially fills the pipe, the conducting sheets are not short circuited.

When the pipeline type is conductive, such as carbon steel or iron, the internal structure is preferably insulated from the pipeline internal surface by an insulating backing. Non-limiting examples of insulating materials suitable for use as insulating backings in the present disclosure are glass, porcelain, plastic or composite polymers. Preferably, the portion of the pipeline in which the conducting sheets are installed include an insulating liner such as a thermoplastic sheet covering the inside circumference of the pipeline under the conducting sheets. When the pipeline section is made of Plexiglas, no insulating backing is needed.

A conductive terminal is 103 installed along the central axial line of the first semi-cylindrical conducting sheet and a corresponding conductive terminal 105 is installed at the central axial line of the second semi-cylindrical conducting sheet, wherein each conductive terminal is placed on the external surface of the pipe section (as shown in FIG. 1C and FIG. 1D) and protrudes through the pipe section to electrically contact a respective semi-cylindrical sheet. The conductive terminal may be insulated from the pipeline by rubber grommets or the like as is known in the art. The conductive terminal is bonded to the semi-cylindrical conducting sheet by any bonding means known in the art, such as solder, conductive epoxy, attaching by screw threads, bolting as several non-limiting examples. The external end of each conductive terminal is attached to wiring (not shown) which connects it to a control unit as described below.

The lengths of the conductive terminals are chosen to provide an external contact, to extend through the pipeline wall and to extend through the insulating material (when used) to contact the semi-cylindrical conducting sheet. In a non-limiting example, when the pipe wall thickness is 20 mm, the conductive terminal may be about 40 mm in length.

When the pipeline type is conductive, the conductive terminals insulated from the pipeline internal surface by a non-conductive bushing. Non-limiting examples of insulating materials suitable for use as insulating bushings in the present disclosure are glass, porcelain, nylon or composite polymers.

The gaps ($2\delta$) at the top and bottom of FIG. 1A separate the two conductive sheets electrically, allowing a charge to build up upon each conductive sheet when equal and opposite voltages are applied at terminals 103 and 105 respectively.

Figure 3:
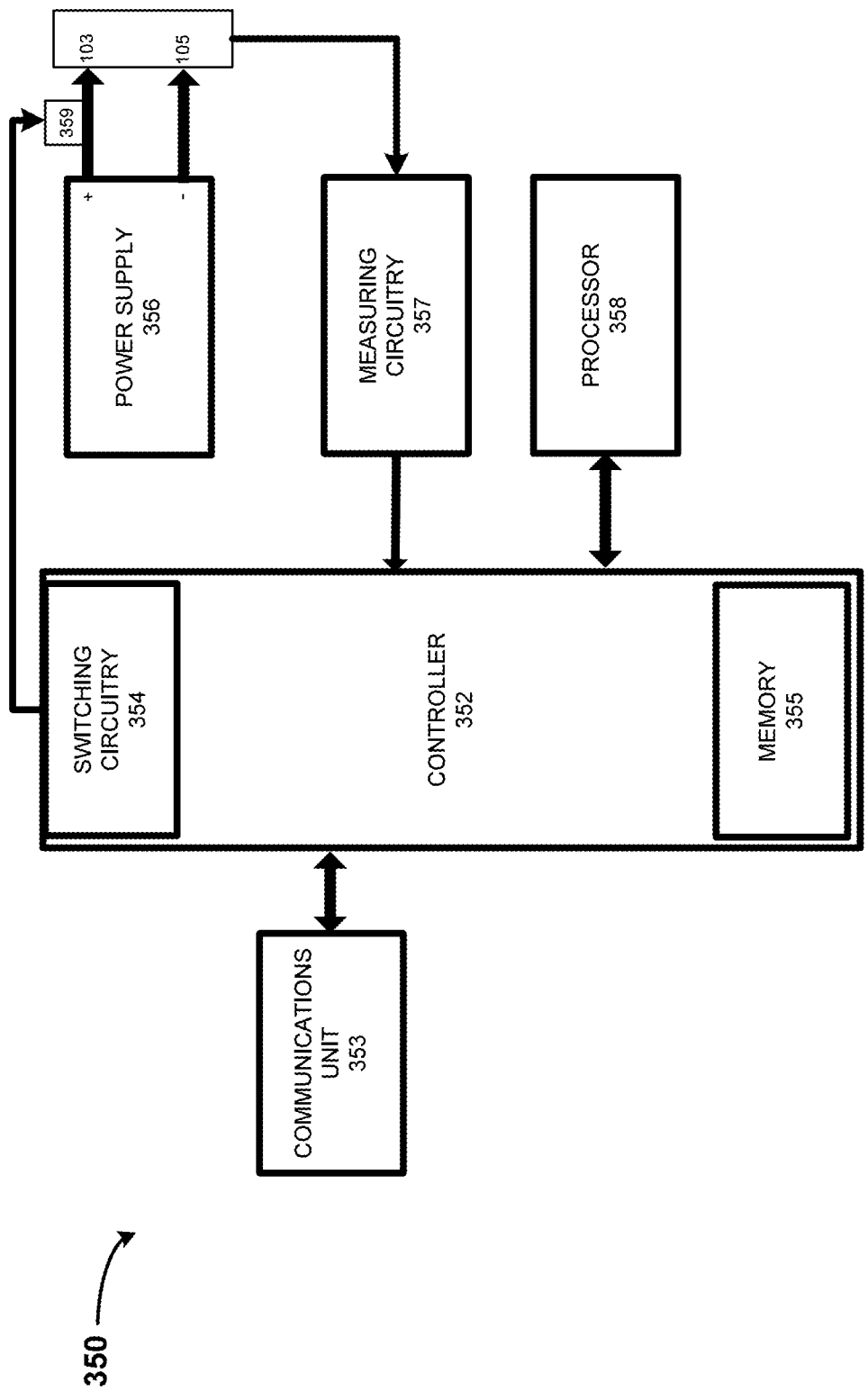
FIG. 3 is an exemplary illustration of a control unit, according to certain embodiments.

A control unit (150, 350) is shown in FIG. 1C and FIG. 3. The control unit includes a power supply 356 to apply a positive DC voltage at the first terminal 103 and a negative DC voltage at the second terminal 105; a switch 359 connected between the power supply 356 and the first terminal 103; a controller 352 having circuitry 354 configured to control the switch; measuring circuitry 357 connected to the conductive terminals 103, 105 to measure the capacitance and resistance between the terminals; processing circuitry 358 configured determine the respective volumes of water, oil and gas in the pipe section based on the capacitance and resistance measurements and to calculate the velocity of the oil flowing in the pipeline.

In a non-limiting example, the controller may include a calibrated LCR meter with a power supply to apply an alternative voltages with f=1-KHz and V0=1 v to first at the second conductive terminals 103, 105. A non-limiting illustration of an LCR meter suitable for performing the measurements at the conductive terminals is shown in FIG. 1G.

The control unit 150a, 150b is located within a recessed compartment on the external surface of the pipe section as shown in FIG. 1C. Wiring (not shown) connects the conductive terminals to the controller. A cover (not shown) protects the control unit, wiring and conductive terminals, and the cover is hermetically sealed to the surface of the pipe section.

Referring to FIG. 1A and FIG. 1C, in order to measure the contents and velocity of the oil at a location on the pipeline, a pipe section 106 is selected which is in a region where the flow is steady, that is, a distance from any source of discontinuity such as pumps or pipe connectors (not shown). The pipe section extends parallel to the ground surface along the z-axis and has a length $z_0$, with a circular cross-section covering the angles from $\phi=0$ to $\phi=2\pi$. At least one section of the pipe is either replaced by the pipe section of the present disclosure or two metal sheets are placed along the inner surface of the existing pipe such that a first sheet 102 covers the angles $\delta<\phi<\pi-\delta$, and extends along the pipe length a distance z, where $0<z<z_o$, while the second sheet 104 covers the angles $\pi+\delta<\phi<2\pi-\delta$, and has a length in the z direction equal to the length z of the first metal sheet. 26 is shown as representing the gap angle separating the two sheets at the each of the top and the bottom of the pipe. Each electrode has radius $\rho=\rho_0$. In a stratified laminar flow, different densities (Table 1) cause distinct separating planes between the phases with water at the bottom and gas at the top, subtended by a phase angle of $\beta_3$ and $\beta_1$, respectively.

In the present disclosure, the volumes of the phase fractions are determined by relating the phase angles with calculated and measured values of capacitances and resistances of the three-phase content. To achieve this using an inclined capacitive plate technique, the surfaces of the electrodes are divided into an N-number of inclined pair of chords. FIG. 1A shows the inclined pair of chords within the water layer (region-III), which are centered at an angle $\beta_{2n}$ and subtended by an angle $2\delta$. For example, the chords of electrode 104 satisfy $\delta \leq \beta_{2n} \leq (\beta_1 - \delta)$ for region I and $(\beta_3 + \delta) \leq \beta_{2n} \leq (\pi - \delta)$ for region III.

FIG. 1A depicts the pipe cross-section with two semi-cylindrical electrodes and the three phase levels of brine (water), oil and gas, each with respect to an angle subtended by an arc from the origin 112 to the interface between two phases. A brine (water)/oil interface 114 is shown at the bottom where an arc is subtended by an angle $\beta_3$ and an oil/gas interface 116 is shown at the top subtended by an angle $\beta_1$ Further, the surface is divided into a number of chords N, where each chord is subtended by an angle $2\delta$ and is centered at an angle $\beta_{2n}$ which varies in accordance with $\beta_1 + \delta \leq \beta_{2n} n \leq \pi/2 - \delta$ for the gas region with similar relation for the brine region. The pipe structure with its conducting internal sheets is depicted in FIG. 1D.

The procedure for measuring the oil, gas and brine volumes is based on the fact that the brine has finite conductivity $\sigma$ and high dielectric constant $\varepsilon_{rb}$, while both oil and the gas have zero conductivity and low dielectric constants, $\varepsilon_{ro}$ and $\varepsilon_{rg}$ respectively. These properties are shown in Table 1.

TABLE 1

Material properties at 25° C. Relative Dielectric Constant ($\varepsilon_r$), Conductivity ($\sigma$), Viscosity (V), Specific Gravity (SG)/Density (D)

| Material | $\varepsilon_r$ | $\sigma$ (S/m) | SG or D(Kg/m³) | V (Pa s) |
|---|---|---|---|---|
| Gas (air) | 1 | $\cong 3 \times 10^{-15}$ | D $\cong$ 1.2 | $\cong 1.8 \times 10^{-5}$ |
| Oil (ESCAID 110) (<PPM 500) | $\cong$2.4 | $\cong 1 \times 10^{-8}$ | SG $\cong$ 0.79-0.81 | $\cong$1.5-1.75 |
| Brine-water | $\cong$78 | $\cong$3.2 | D $\cong$ 1010 | $\cong 1 \times 10^{-3}$ |

Applying a DC voltage across the poles (103, 105) of the two sheets as shown in FIG. 1D enables the measuring circuitry 357 to measure the resistance caused by the brine/water volume.

The processing circuitry is configured to calculate the capacitance using the resistance measurements by using the equations:

$$C = \frac{\varepsilon_0 \varepsilon_r}{2_{\phi 0}} \ln\left(\frac{b}{a}\right) F/m$$

and $$R = \frac{\varepsilon_0 \varepsilon_r}{C\sigma},$$

wherein $\sigma$ is the conductivity of the brine or water; $\varepsilon_0$ is the dielectric constant of water; and $\varepsilon_r$ is the relative dielectric constant of the brine, wherein $\delta$ is the angle subtended by a sector from the center of the pipe section to the edge of the gap; N is the number of chords subtended by an angle $2\delta$, wherein N is an even number and an integer; $\beta 1$ is the angle from the center of the pipe section to the top of the oil volume, $\beta 2$ is the angle from the center of the pipe section to the top of the water volume and $a_n = \rho_0^* \{\text{Cos}(\delta)\text{cot}(\beta_{2n}) - \text{Sin}(\delta)\}$ $b_n = \rho_0^* \{\text{Cos}(\delta)\text{cot}(\beta_{2n}) + \text{Sin}(\delta)\}$ $\beta_{2n} = (2n+1)\delta$ radians, with n=0, 1, 2 ... N, $$N = \left(\frac{90°}{2\delta}\right) - 1$$

and $\phi_n = \beta_{2n}$ radians;

The processor 358 is configured to analyze the measurements and calculate the total resistance and the total capacitance of the semi-cylindrical sheets based on the following equations:

$$R_T = \sum_1^N \left(\frac{1}{\sigma}\right) 2_{\phi n} / \ln(b_n/a_n) \Omega/m$$

and $$C_T = \sum_{n=0}^N \left(\frac{\varepsilon_0 \varepsilon_r}{2_{\phi n}} \ln\left(\frac{b_n}{a_n}\right)\right) \frac{F}{m°}$$

The processing circuitry is further configured to determine the capacitance measurement based on equation (2):

$$C_w = \varepsilon_0 \varepsilon_{rb}/(\sigma R) \text{Farad}/m \quad (2)$$

wherein $\varepsilon_0 = 8.854 \, e{-12}$, $\sigma(s/m)$ is the conductivity of the element under measurement; $\varepsilon_{ro}$ is to the dielectric constant of the oil; and $\varepsilon_{rb}$ is the dielectric constant of the brine and 'a' and 'b' dimensions are shown in FIG. 1A.

Figure 2A:
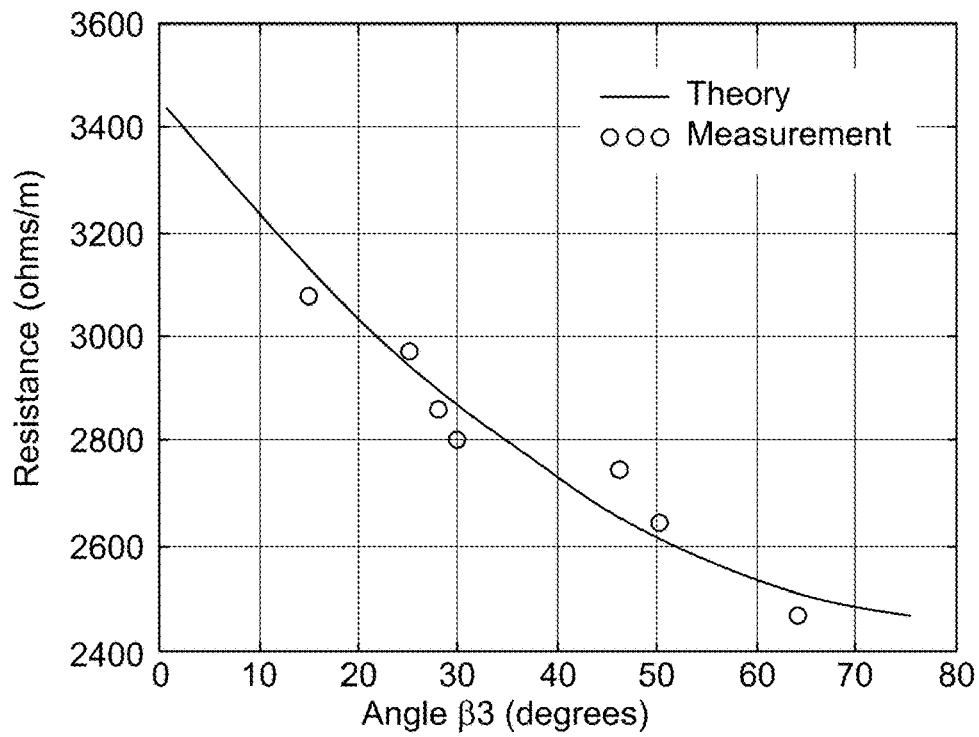
FIG. 2A is a chart of brine resistance versus water-oil angle θ3, according to certain embodiments
Figure 2B:
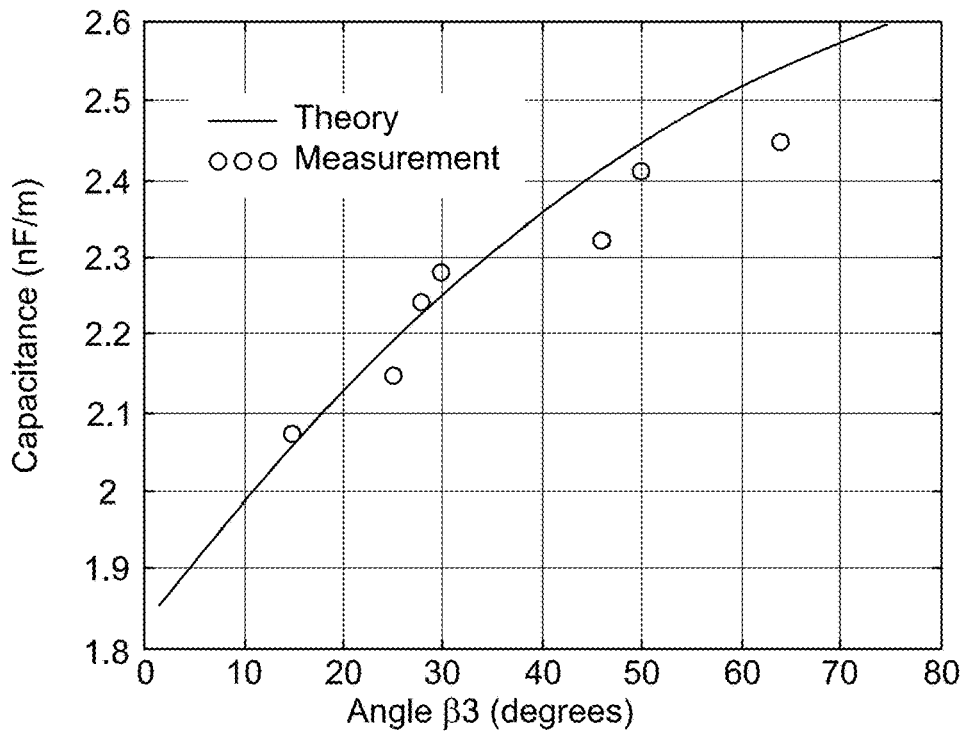
FIG. 2B is a chart of equivalent capacitance in nanofarads per meter versus water-oil angle β3, according to certain embodiments.

FIG. 2A depicts a plot of the relationship between the brine heights in terms of the angle $\beta 3$ and its effective resistance Rp (ohms/m) along with experimental values. FIG. 2B shows the brine capacitance per meter of the brine with the brine heights represented by the angle $\beta 3$.

Figure 2C:
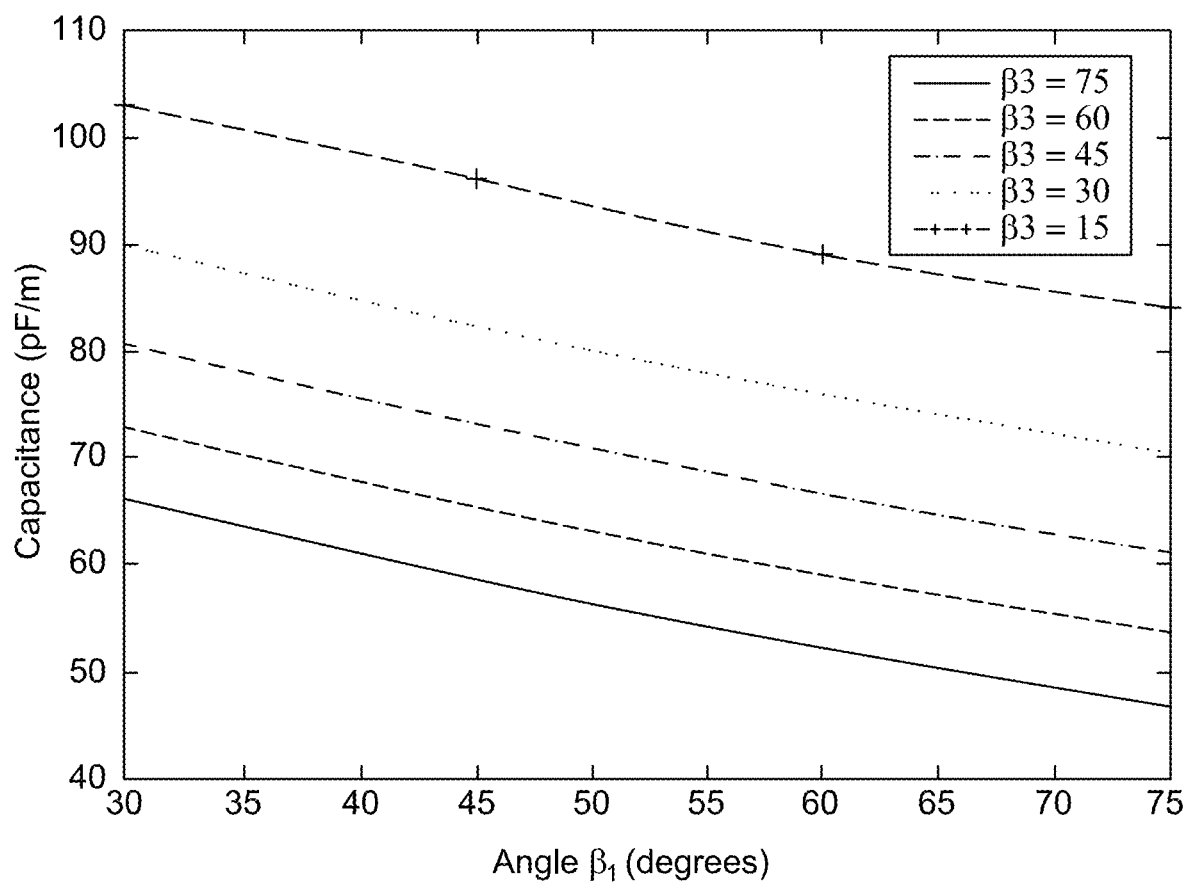
FIG. 2C is a chart of capacitance of the gas ($C_p$) in picofarads per meter versus the oil/gas angle β1 for different values of β3, according to certain embodiments.

The total capacitance Cp (F/m) of the oil-gas-brine mixture between the two conducting sheets is measured by the measuring circuitry 357 shown in FIG. 3, which represents the parallel capacitances of the three layers. This capacitance is equal to the sum of Cg, Co, and Cw, which are the capacitance of the gas, the oil and the water in the pipe section in Farads per meter. Since Cw was previously calculated, the value of the sum of Cg+Co is easily determined. The plot of the Cg versus the heights of the gas (represented by the angle $\beta 1$ for different values of $\beta 3$ is shown in FIG. 2C. This will solve for the angle $\beta 1$ and hence the heights of the oil, gas and water in the pipe are readily obtained.

Figure 2D:
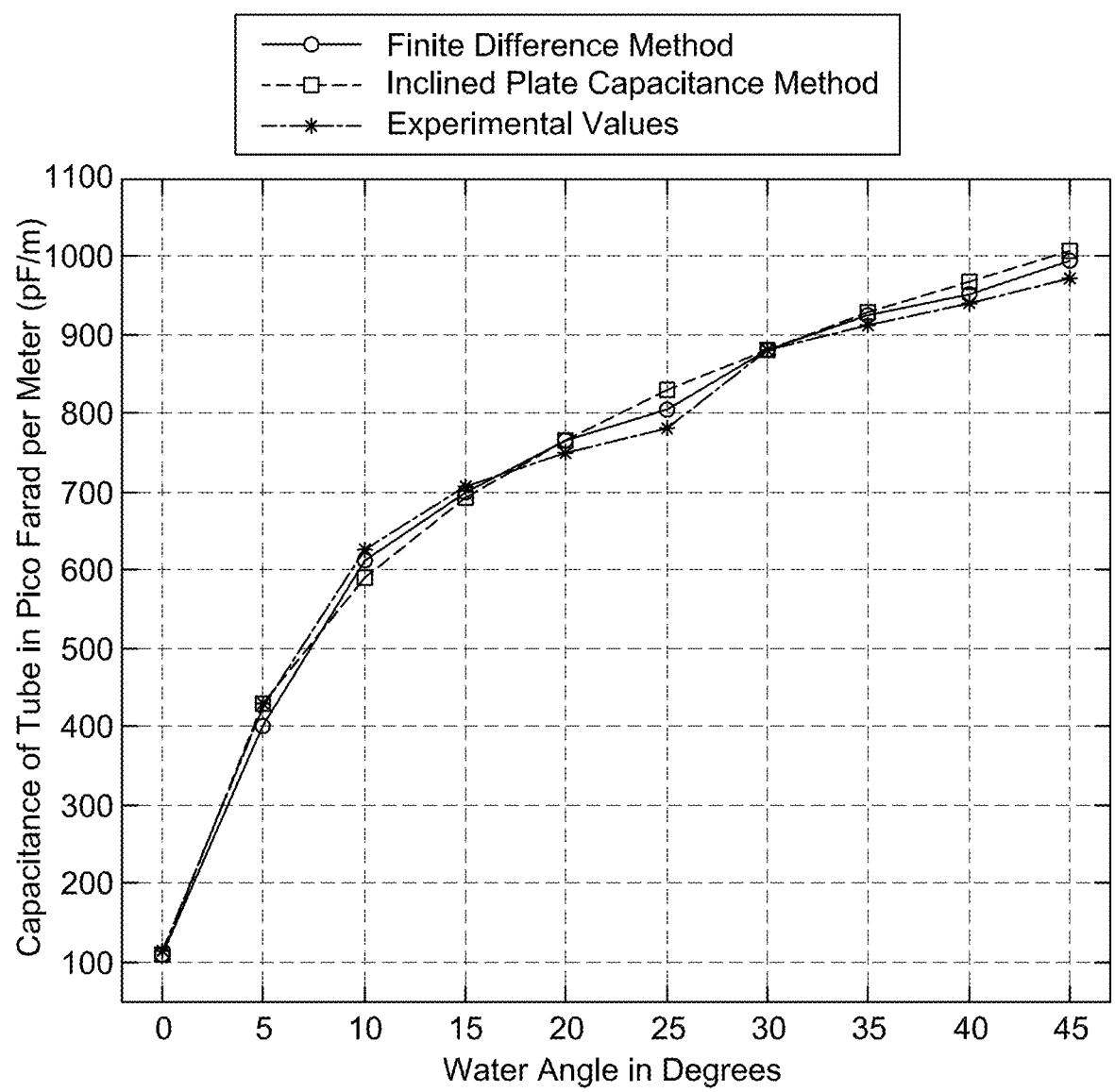
FIG. 2D is chart of overall capacitance in picofarads per meter when the pipe is partially filled with brine. Comparison between Finite Difference, the present technique and the experimental results is shown.

FIG. 2D depicts the total capacitance when the pipe is partially filled with brine and the comparison with a prior art Finite Difference method and an inclined plate capacitance method, both detailed by Iqbal (See M. S. Iqbal, "Novel metering system for the three phase flow in horizontal oil pipes under steady flow", 2018 Texas Symposium on Wireless and Microwave Circuits and Systems (WMCS), INSPEC Accession No. 17880625 DOI: 10.1109/WM-CaS.2018.8400621 April 2018, herein incorporated by reference in its entirety), and the experimental results obtained by the present disclosure.

Figure 2E:
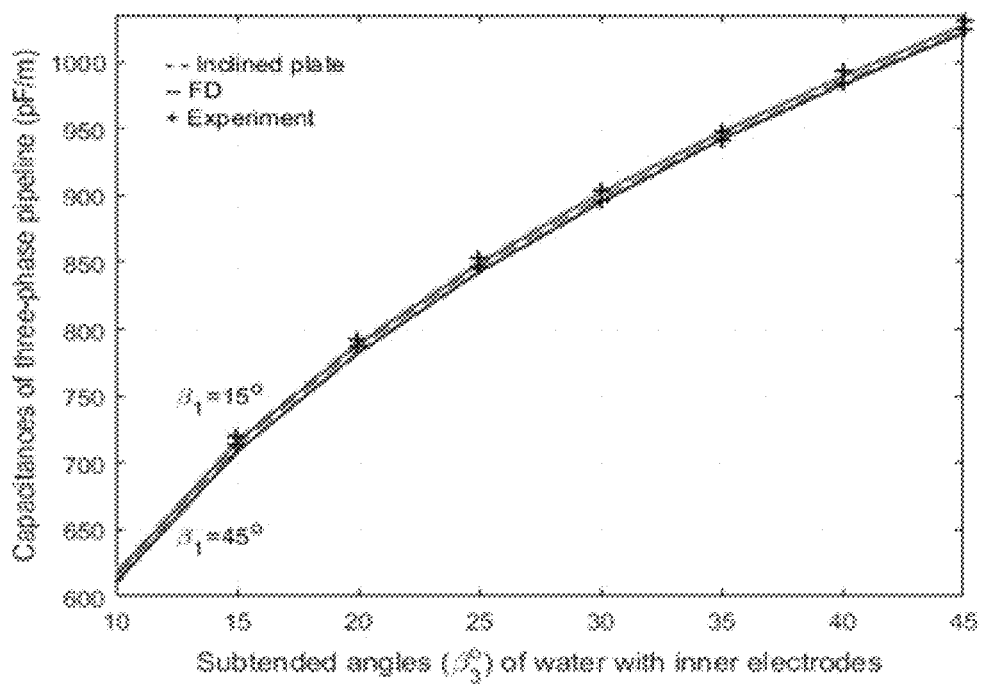
FIG. 2E is a chart comparing calculated, measured and referenced values of total capacitance (internal electrodes) versus water phase-angle.
Figure 2F:
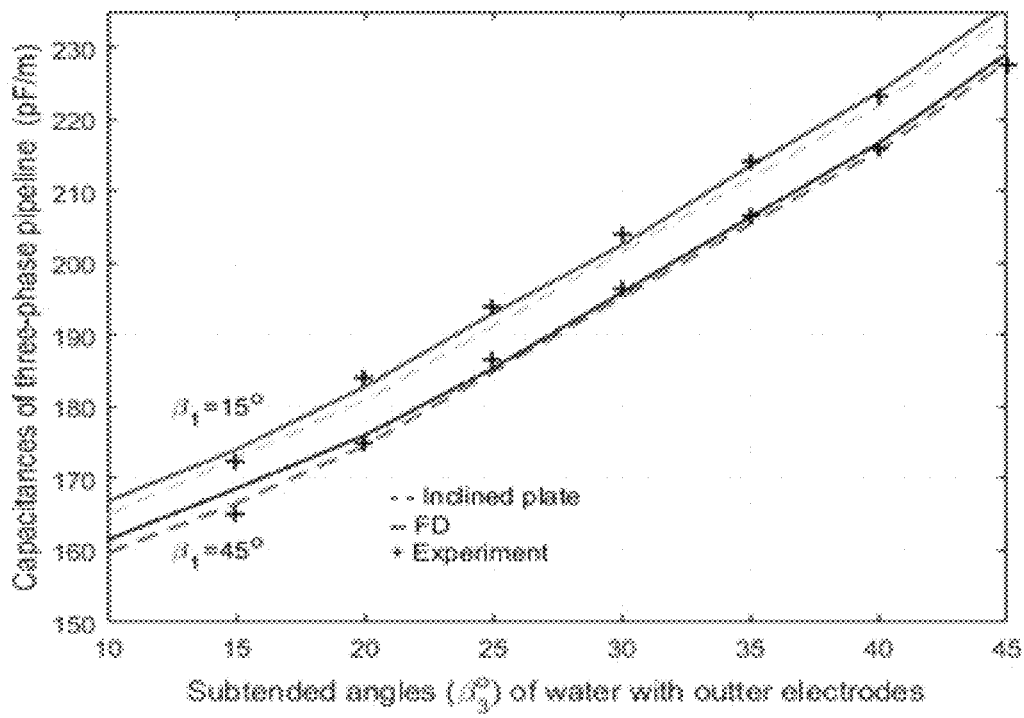
FIG. 2F is a chart comparing calculated, measured and referenced values of total capacitance (external electrodes) versus water phase-angle.

FIG. 2E and FIG. 2F show comparisons of experimental results versus inclined plate measurements and finite difference results of the prior art. It is clear from the comparisons that the internal structure of the present disclosure more accurately measures the resistance and capacitance of the water layer. These results are shown in Table 2.

TABLE 2

Calibration to known and measured values

| Electrode-location | Calculated Cap. (Eq.11) | Known Capacitances | Finite Difference Method |
|---|---|---|---|
| Semi-cylindrical capacitor with 100% gas contents | | | |
| Inside pipeline surface (FIG. 1) | 104.9 pF/m 117.69 pF/m | 104.95 pF/m | 103.43 pF/m |
| Outside pipeline surface | | 117.08 pF/m | 116.41 pF/m |
| Semi-cylindrical capacitor with $\beta_3 = 45°$ water contents | | | |
| Inside pipeline surface (FIG. 1) | 1001.9 pF/m | 958 pF/m | 999.9 pF/m |
| Outside pipeline surface | 212.7 pF/m | 215.8 pF/m | 214.8 pF/m |

A second pipe section 108 having a second internal structure installed at a second location within the pipeline is installed at a distance (d) from the first internal structure 106 as shown in FIG. 1C.

In order to calculate the oil volume flowing in the pipe, the velocity of the flow inside the pipe must be measured. Second capacitance measurements are made at the second location at a time ($\tau_0$), wherein ($\tau_0$) is the time elapsed between a capacitance measurement at the first location and a capacitance measurement at the second location. The velocity is calculated by cross correlating between the measured Cp at two different locations, represented by 106 and 108 in FIG. 1C, along the pipe separated by a distance 'd' to determine the time '$T_0$' elapsed between two similar Cp values. The velocity equals $d/T_0$.

The processing circuitry is configured to calculate the velocity of the oil flowing in the pipeline based on the equation velocity=$d/\tau_0$ and the capacitance measurements of the first pipe section and the second capacitance measurements of the second pipe section, based on the equation:

$$\text{Volume of } \frac{\text{oil}}{\text{time}} = (\pi * \text{Rad}^2 - V_g - V_w) * \text{velocity},$$

wherein Rad is the pipe radius and Vg, and Vw are the gas and water volumes respectively, given by:

$$V_g = \beta_1 \times \text{Rad}^2 - \text{Rad}^2 \times \cos(\beta_1) \times \sin(\beta_1)$$

$$V_b = \beta_3 \times \text{Rad}^2 - \text{Rad}^2 \times \cos(\beta_3) \times \sin(\beta_3).$$

During the measurement, the pressure of the oil pump (see FIG. 5A) is increased in order to generate a surge in the flow which travels along the pipe and can be detected by measured values of the capacitance.

The control unit 350 further includes a communications unit 353 having communications circuitry capable of transmitting the measurements of the volumes of water, oil and gas in the pipe section and the velocity of the oil flowing in the pipeline between the first and second pipe sections to a remote control center using wired or wireless communications.

Figure 4:
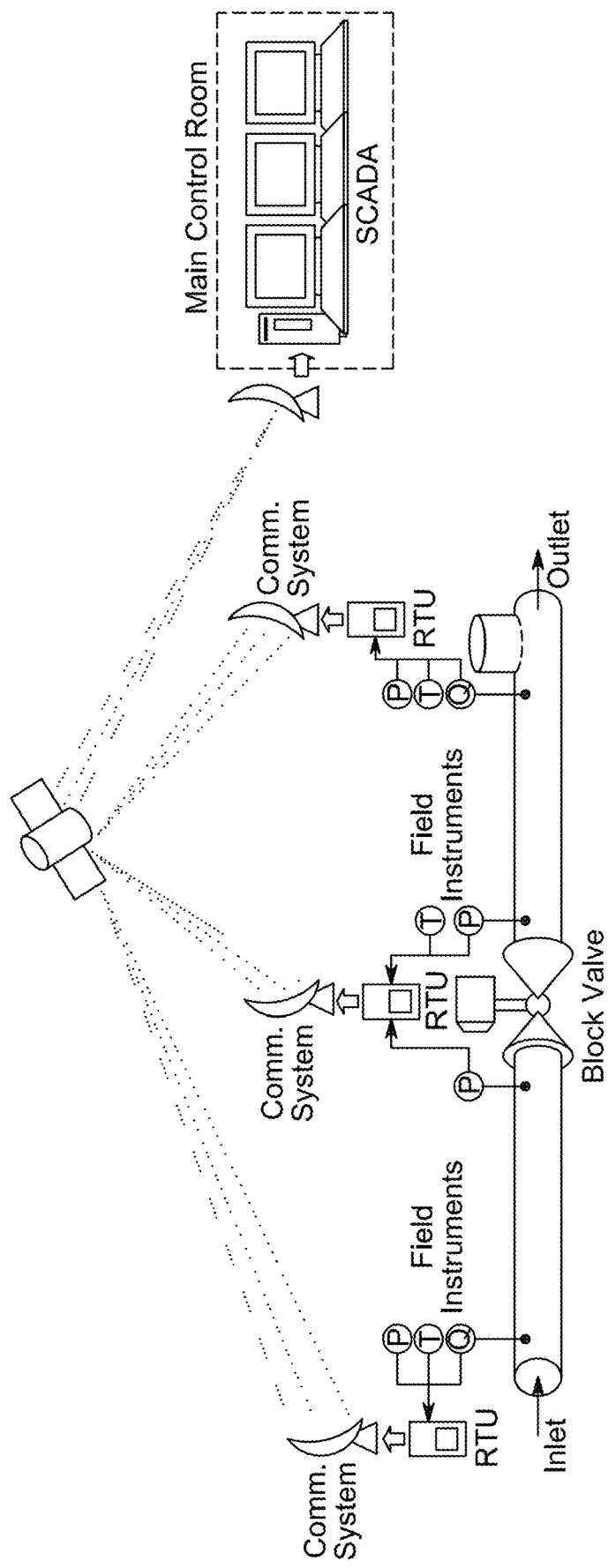
FIG. 4 illustrates in an example of a pipeline section having a remote transmission unit, according to certain embodiments.

The measurements may be transmitted along the pipeline through wires embedded within the plurality of pipeline sections. Remote terminal units (RTU), as shown in FIG. 4, may be placed along the pipeline to receive the measurements. The measurements are transmitted to a satellite then to a remote control center (Main Control Room) and analyzed using SCADA software.

The remote terminal unit transmits the measurements to the remote control center by wireless communication, wherein the wireless communication is at least one of microwave communications (WiMAX), 3G, 4G, LTE, Wifi, LAN, VLAN, WAN and satellite communications.

FIG. 5 shows an exemplary wireless access network (WAN) used at a pump station to transmit data. The pump station is an example of an RTU.

Figure 6:
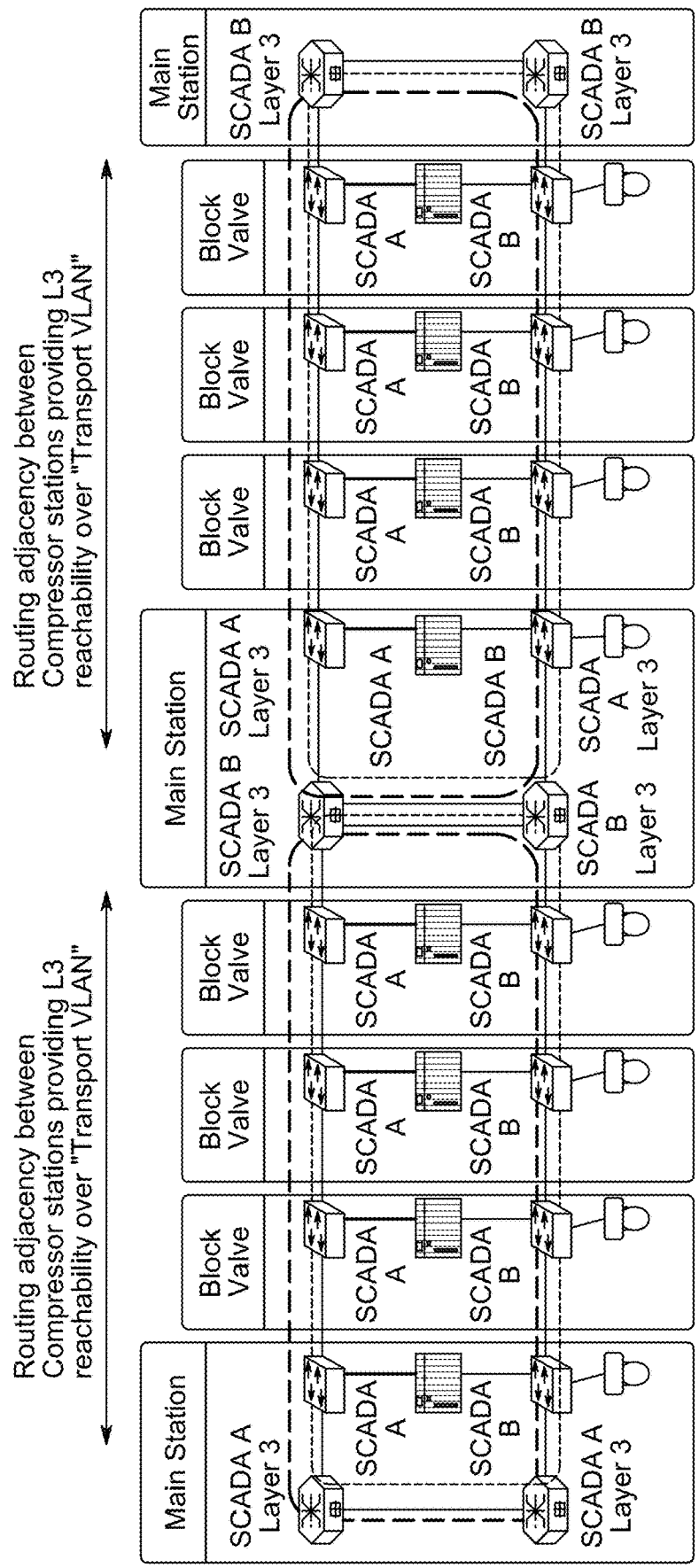
FIG. 6 illustrates an example of a pipeline using VLAN communications and SCADA control, according to certain embodiments.

FIG. 6 shows a pipeline system linking block valves having SCADA controllers which transmit block valve measurements over a virtual LAN (VLAN).

The present invention is not limited to only the two pipeline sections having internal structures. The pipeline may have a plurality of pipe sections placed along the length z of the pipeline so that multiple measurements of the heights of the water, oil and gas and the oil velocity may be taken. The measurements may be transmitted to the remote control center with an identification of the location of each pipe section and other information, such as temperature, wind velocity, damage taken by other sensors in the pipe section.

A second embodiment of a method for measuring the water, oil and gas volumes within a cylindrical horizontal pipeline and the velocity of the oil flowing in the pipeline, wherein the pipeline has a circular cross-sectional area of radius (Rad), and an axial length (Z) is described with respect to FIG. 1A-FIG. 1E.

The method comprises installing, within the pipeline having a plurality of pipe sections (106, 108), at least one pipe section having an internal structure including a first semi-cylindrical conducting sheet 102 covering a portion of the internal surface of the pipe section and a second semi-cylindrical conducting sheet 104 covering an opposing portion of the internal surface of the section of the pipe section, wherein each semi-cylindrical sheet has radius (Rad) and axial length $z_0$, so that a gap ($2\delta$) exists between an edge of the first semi-cylindrical conducting sheet and a corresponding edge of the second semi-cylindrical conducting sheet.

The method continues by installing a first conductive terminal 103 along the central axial line of the first semi-cylindrical conducting sheet and a second conductive terminal 105 at the central axial line of the second semi-cylindrical conducting sheet so that each conductive terminal is located on the external surface of the pipe section and protrudes through the pipe section to electrically contact a respective semi-cylindrical sheet, then connecting the conductive terminals to a control unit 350, as shown in FIG. 3, including a controller 352 having circuitry configured for applying a positive DC voltage at the first terminal and a negative DC voltage at the second terminal and for measuring the resistance at the conductive terminals. The control unit further has a processor 358 having processing circuitry configured for determining the respective volumes of water, oil and gas in the pipe section and calculating the velocity of the oil flowing in the pipeline. The control unit measures the resistance across the semi-cylindrical electrodes.

The processing circuitry is configured for calculating the capacitance of the water layer based on the measured resistance and the equations:

$$C = \frac{\varepsilon_0 \varepsilon_r}{2\phi_0} \ln\left(\frac{b}{a}\right) F/m$$

and the relationship $$R = \frac{\varepsilon_0 \varepsilon_r}{C\sigma},$$

where R and C are the resistance and capacitance of the water layer, wherein $\varepsilon_0$=8.854 e−12, $\sigma$(s/m) is the conductivity of the element under measurement; $\varepsilon_r$ is the dielectric constant of the phase under measurement, and "a", "b" and $\phi_0$ are measurements as shown in FIG. 1A.

The method continues by calculating the total resistance and the capacitances of the semi-cylindrical sheets based on the following equations:

$$R_T = \sum_1^N \left(\frac{1}{\sigma}\right) 2_{\phi n} / \ln(b_n/a_n) \Omega/m$$

$$\text{and } C_T = \sum_{n=0}^N \left(\frac{\varepsilon_0 \varepsilon_r}{2_{\phi n}} \ln\left(\frac{b_n}{a_n}\right)\right) F/m$$

where $a_n = \rho_0 * \{\cos(\delta)\cot(\beta_{2n}) - \sin(\delta)\}$ $b_n = \rho_0 * \{\cos(\delta)\cot(\beta_{2n}) + \sin(\delta)\}$ $\beta_{2n} = (2n+1)\delta$ radians, with n=0, 1, 2 . . . N, $$N = \left(\frac{90°}{2\delta}\right) - 1$$

and $\phi_n = \#_{2n}$ radians and wherein $\delta$ is the angle subtended by a sector from the center of the pipe section to the edges of the gap; "N" is the number of pairs of chords subtended by an angle $2\delta$, $\beta 1$ is the angle from the center of the pipe section to the top of the oil volume, $\beta 2$ is the angle from the center of the pipe section to the top of the water volume, $\rho_0$=the radius of a chord from the axial center of the internal structure as shown in FIG. 1A.

The method continues by calculating, by the processing circuitry, the respective heights of the water, oil and gas within the pipe section, wherein the volume of water is defined as having a height (hw) measured along the vertical radius of the cross section of the pipe section, the oil content is defined as having a height (ho) measured along the vertical radius of the cross section of the pipe section and the gas is defined as having a height (hg) measured along the vertical radius of the cross section of the pipe section, wherein 2Rad=hw+ho+hg.

The method further continues by installing a second pipe section 108 having a second internal structure at a second location within the pipeline, the second internal structure separated by a distance (d) from the first internal structure as shown in FIG. 1C.

The method proceeds by measuring a second capacitance and a second resistance at the second location at a time ($\tau_0$), wherein ($\tau_0$) is the time elapsed between a capacitance measurement at the first location and a capacitance measurement at the second location, and calculating, by the processing circuitry, the velocity of the oil flowing in the pipeline based on the equation velocity=d/$\tau_0$ and the capacitance and resistance measurements of the first pipe section and the second capacitance and second resistance measurements of the second pipe section.

Calculating by the processing circuitry of the volume of oil flowing per unit time, is based on the equation:

$$\text{Volume of } \frac{\text{oil}}{\text{time}} = (\pi * \text{Rad}^2 - V_g - V_w) * \text{velocity},$$

wherein Rad is the pipe radius and Vg, and Vw are the gas and water volumes respectively, given by:

$V_g = \beta 1 \times \text{Rad}^2 - \text{Rad}^2 \times \cos(\beta 1) \times \sin(\beta 1)$ $V_b = \beta 3 \times \text{Rad}^2 - \text{Rad}^2 \times \cos(\beta 3) \times \sin(\beta 3)$ Once the heights of the water, oil and gas and velocity of oil in the pipeline are determined, the method proceeds by transmitting, by communications circuitry in the control unit 350, the measurements of the volumes of water, oil and gas in the pipe section and the velocity of the oil flowing in the pipeline between the first and second sections to a remote control center using wired or wireless communication. As described with respect to the first embodiment and shown in FIG. 4, FIG. 5B, and FIG. 6, the communication may be partially through wires embedded in the plurality of pipeline sections. The wires may connect to a remote terminal unit (RTU), wherein the remote terminal unit transmits the measurements to a remote control center by wireless communication, wherein the wireless communication is at least one of microwave communications (WiMAX), 3G, 4G, LTE, Wifi, LAN, WAN and satellite communications.

A third embodiment to a non-transitory computer readable medium is described with reference to FIG. 1A to FIG. 3, the non-transitory computer readable medium having instructions stored therein that, when executed by one or more processors, causes the one or more processors to perform a method for measuring the water, oil and gas volumes within a cylindrical horizontal pipeline and the velocity of the oil flowing in the pipeline, wherein the pipeline has a circular cross-sectional area of radius (Rad), and an axial length (Z), the pipeline having a plurality of pipe sections (106, 108, for example), at least one pipe section having an internal structure including a first semi-cylindrical conducting sheet 102 covering a portion of the internal surface of the pipe section and a second semi-cylindrical conducting sheet 104 covering an opposing portion of the internal surface of the pipe section, wherein each semi-cylindrical sheet has radius (Rad) and axial length $z_0$, so that a gap ($2\delta$) exists between an edge of the first semi-cylindrical conducting sheet and a corresponding edge of the second semi-cylindrical conducting sheet, and a first conductive terminal 103 installed along the central axial line of the first semi-cylindrical conducting sheet and a second conductive terminal 105 installed at the central axial line of the second semi-cylindrical conducting sheet so that each conductive terminal is located on the external surface of the pipe section and protrudes through the pipe section to electrically contact a respective semi-cylindrical sheet.

The method of the third embodiment comprising applying a positive DC voltage at the first terminal and a negative DC voltage at the second terminal, the conductive terminals connected to a control unit; measuring, by a controller in the control unit and having circuitry configured for measuring, the resistance at the first and second terminals; calculating, by processing circuitry in the control unit, the capacitance based on the measured resistance and the equations:

$$C = \frac{\varepsilon_0 \varepsilon_r}{2\phi_0} \ln\left(\frac{b}{a}\right) F/m$$

and the relationship $$R = \frac{\varepsilon_0 \varepsilon_r}{C\sigma},$$

determining, the respective volumes of water, oil and gas in the pipe section and calculating the velocity of the oil flowing in the pipeline; analyzing, by the processing circuitry, the total resistance and total capacitance of the semi-cylindrical sheets based on the equations:

$$R_T = \sum_1^N \left(\frac{1}{\sigma}\right) 2\phi_n / \ln(b_n/a_n) \quad \Omega/m \quad \text{and}$$

$$C_T = \sum_{n=0}^N \left(\frac{\varepsilon_0 \varepsilon_r}{2\phi_n} \ln\left(\frac{b_n}{a_n}\right)\right) \quad F/m$$

wherein δ is the angle subtended by a sector from the center of the pipe section to the edges of the gap; N is the number of chords subtended by an angle 2δ, wherein N=0, 1, 2, . . . N; β1 is the angle from the center of the pipe section to the top of the oil volume, β2 is the angle from the center of the pipe section to the top of the water volume and pipe section to the top of the water volume and $a_n = \rho_0 * \{Cos(\delta)cot(\beta_{2n}) - Sin(\delta)\}$ $b_n = \rho_0 * \{Cos(\delta)cot(\beta_{2n}) + Sin(\delta)\}$ $\beta_{2n} = (2n+1)\delta$ radians, with n=0, 1, 2 . . . N, $$N = \left(\frac{90°}{2\delta}\right) - 1$$

and $\phi_n = \beta_{2n}$ radians;

determining, by the processing circuitry, the capacitance of the water, the water including brine, based on the equation:

$Cw = \varepsilon_o \varepsilon_{rb}/(\sigma R)$ Farad/$m$ wherein σ is the conductivity of the brine or water; C is the dielectric constant of the oil; and $\varepsilon_{rb}$ is the dielectric constant of the brine; defining, by the processing circuitry, the volume of water as having a height (hw) measured along the vertical radius of the cross section of the pipe section, the oil content as having a height (ho) measured along the vertical radius of the cross section of the pipe section, the gas as having a height (hg) measured along the vertical radius of the cross section of the pipe section, wherein 2Rad=hw+ho+hg, and calculating, by the processing circuitry, the respective heights of the water, oil and gas within the pipe section; measuring at a time (τ0), second capacitance and second resistance at a second pipe section having a second internal structure and located at a second location within the pipeline, the second internal structure separated by a distance (d) from the first internal structure, wherein (τ$_0$) is the time elapsed between a capacitance measurement at the first location and a capacitance measurement at the second location, and calculating, by the processing circuitry, the velocity of the oil flowing in the pipeline based on the equation velocity=d/τ$_0$, the capacitance and resistance measurements of the first pipe section and the second capacitance and second resistance measurements of the second pipe section; calculating, by the processing circuitry, the volume of oil flowing per unit time, based on the equation:

$$\text{Volume of } \frac{\text{oil}}{\text{time}} = (\pi * \text{Rad}^2 - V_g - V_w) * \text{velocity},$$

wherein Rad is the pipe radius and Vg, and Vw are the gas and water volumes respectively, given by:

$V_g = \beta 1 \times \text{Rad}^2 - \text{Rad}^2 \times \cos(\beta 1) \times \sin(\beta 1)$ $V_b = \beta 3 \times \text{Rad}^2 - \text{Rad}^2 \times \cos(\beta 3) \times \sin(\beta 3)$ The third embodiment continues by transmitting, by communications circuitry in the control unit, the measurements of the volumes of water, oil and gas in the pipe section and the velocity of the oil flowing in the pipeline between the first and second pipe sections to a remote control center using wired or wireless communication.

Figure 1E:
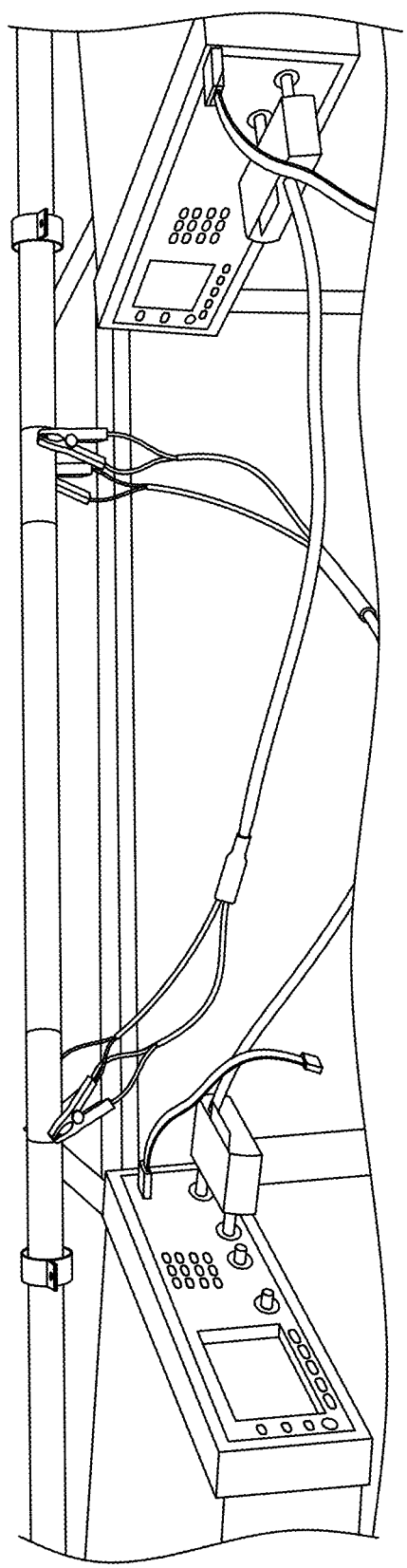
FIG. 1E depicts an experimental testing arrangement, according to certain embodiments.
Figure 5A:
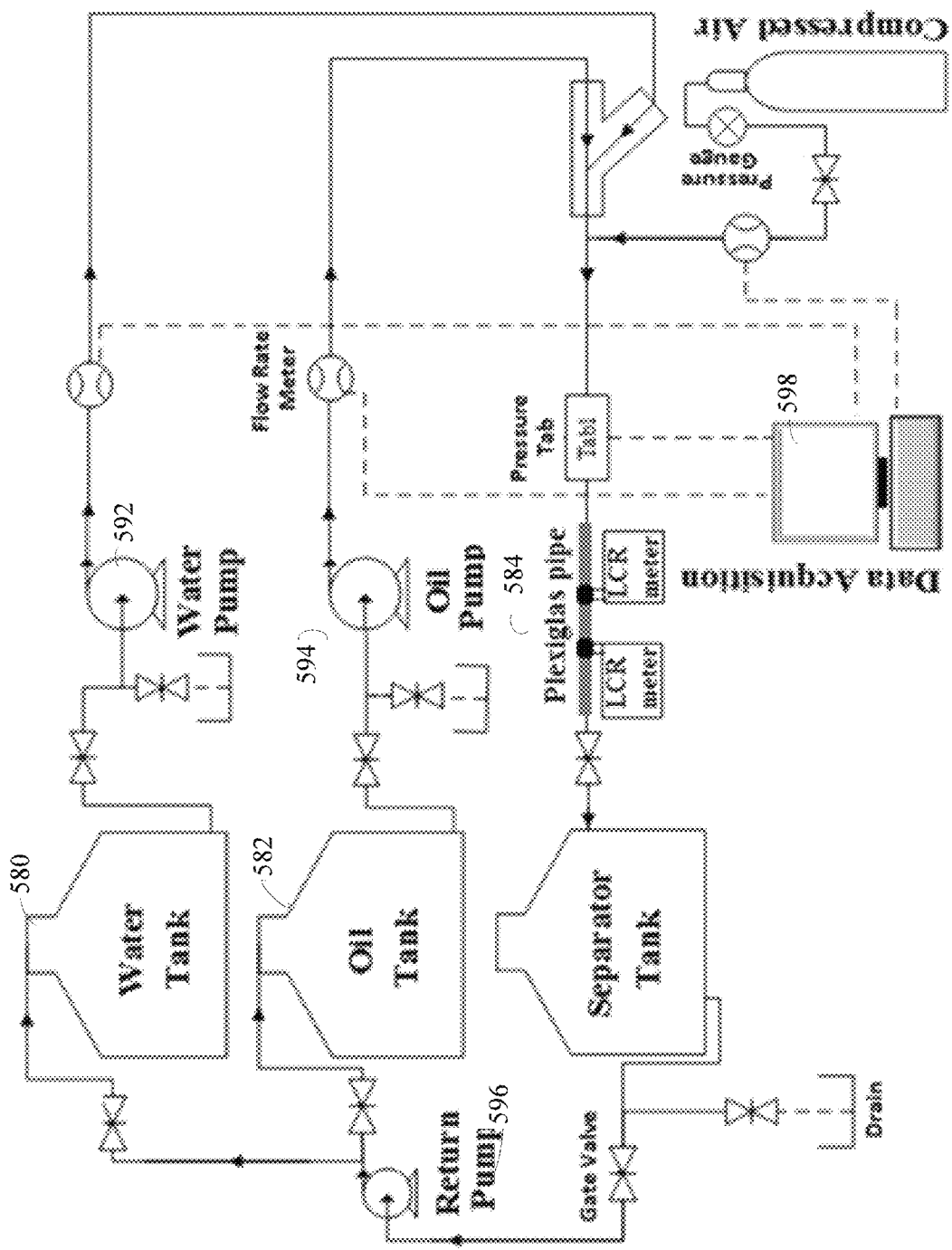
FIG. 5A is a schematic diagram of the flow rate measurement setup, according to certain embodiments.
Figure 5B:
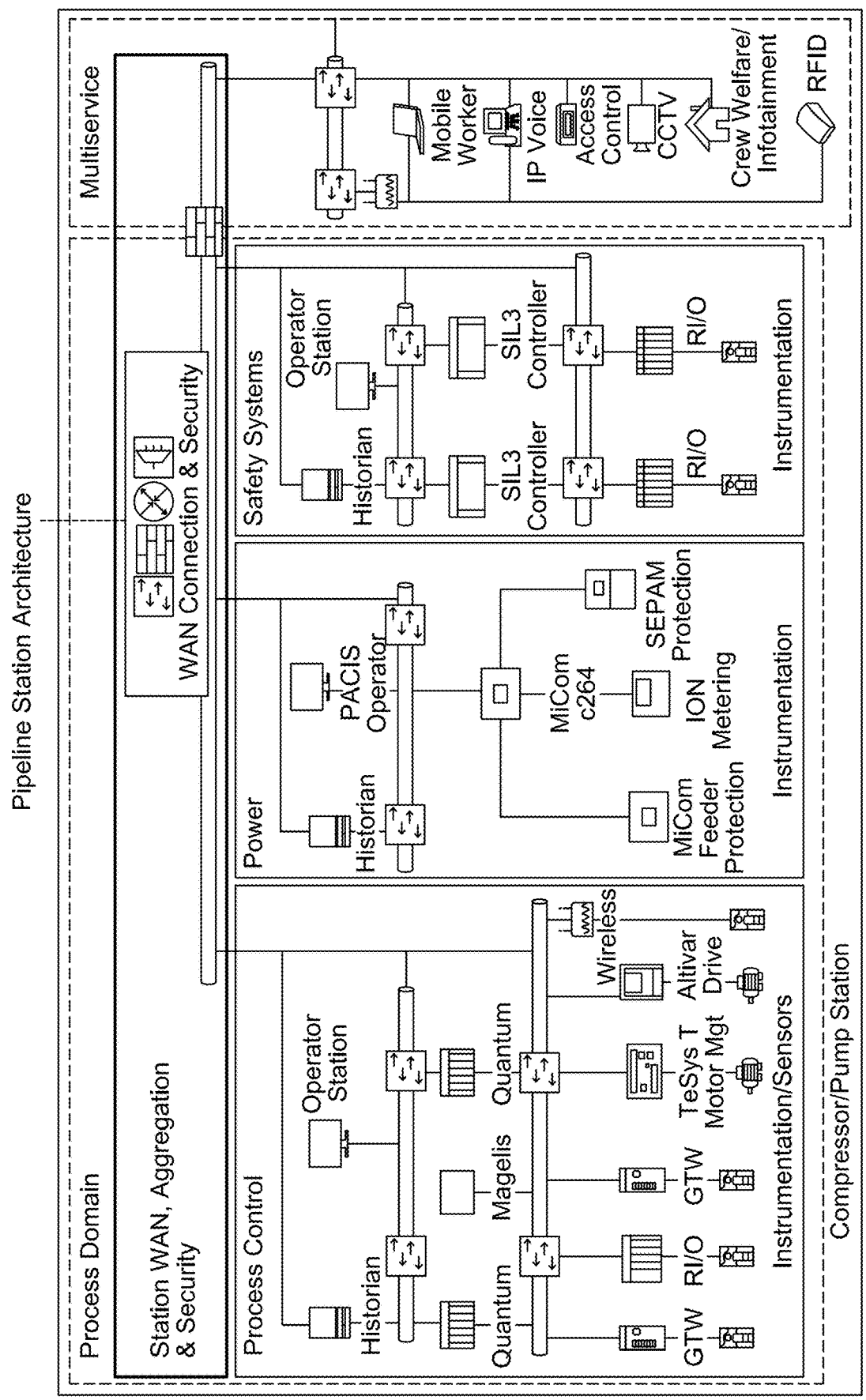
FIG. 5B illustrates an example of a pump station using a WAN, according to certain embodiments.

A fourth embodiment to an experimental arrangement for measuring the flow rate of a three phase pipeline is described with respect to FIG. 5A. The arrangement comprises a water supply tank 580, an oil supply tank 582, a Plexiglas pipe section 584, a water pump 592, an oil pump 594, a return pump 596 and a data acquisition system 598. FIG. 1E shows an image of the Plexiglas pipe with two integrated semi-cylindrical capacitors, where the length, gap, and separation (d) of the electrodes are selected to optimize the capacitance measurement. The bottom gap of the electrodes, which remains submerged in the conductive water layer, is insulated using sand-glue. To determine the estimated velocity of the fluid flow, capacitances of both set of electrodes are recorded and cross-correlated to determine the time delay (T$_O$) needed for a certain wavy point of the flow to pass through both capacitors. Thus, the velocity is calculated by 'd/T$_O$' and the volume flowing per unit time is given by, Volume of oil/time=$(\pi \times \text{Rad}^2 - V_g - V_w) \times$velocity $V_g = \beta 1 \times \text{Rad}^2 - \text{Rad}^2 \times \cos(\beta 1) \times \sin(\beta 1)$ $V_w = \beta 3 \times \text{Rad}^2 - \text{Rad}^2 \times \cos(\beta 3) \times \sin(\beta 3)$ where 'Rad' is the pipe radius, $V_g$ and $V_w$ are the volumes and $\beta_1$ and $\beta_3$ are phase-angles of the gas and water regions, respectively.

In a non-limiting example, an experimental testing arrangement includes two 1963-liter supply-tanks, a 60 cm long, 1.6 cm radius Plexiglas pipeline and three single-stage 3.5-hp end-suction centrifugal supply/return pumps. Using a data acquisition system, the maximum laminar flow rates achieved for water, oil and air are 0.04 m3·min−1, 0.04 m3·min−1 and 0.9 m3.min−1, respectively. In a non-limiting example, the data acquisition system is LabView. FIG. 1E shows the zoomed image of the Plexiglas pipe with two integrated semi-cylindrical capacitors, where the length, gap, and separation (d) of the electrodes are selected to be 15 cm, 1 mm and 60 cm, respectively. The bottom gap of the electrodes, which remains submerged in the conductive water layer, are insulated using sand-glue.

In a non-limiting example, a Plexiglas ($\varepsilon_r$=2.7) pipeline with thickness t=0.15 mm, electrode length ($Z_O$)=20 cm, (in z-axis), angle δ=0.25° and N=179, the total capacitance and total resistance equations above are used to calculate the total resistance and capacitance of a three-phase near-horizontal pipeline with stratified flow. Referring to Table 1, the water region has highest σ and highest $\varepsilon_r$, thus the three parallel conducting paths between the two electrodes are mostly dominated by the water layer. Thus, the total resistance between the electrodes are equivalent to the resistance of the water layer ($R_T \cong R_W$). FIG. 2A plots the calculated resistance curve of a partially water filled semi-cylindrical capacitor for different levels of water. This response is related to electrodes mounted within the pipe surface and demonstrates an inversely proportional relationship between the resistance and water phase angle $\beta_3$.

Experimental measurements are described below and a comparison is made to prior art measurements.

In a non-limiting example, measurements were taken on a pipe of radius 3.2 cm and length 150 cm. The measurements for Cp and Rp are normalized to a 1 m length. In a further non-limiting example, measurements were repeated for a pipe of length 25 cm and radius 8 cm. There was agreement between the theory and the experiments as well as with the finite difference (FD) method described by Iqbal. (See M. S. Iqbal, "Novel metering system for the three phase flow in horizontal oil pipes under steady flow", 2018 Texas Symposium on Wireless and Microwave Circuits and Systems (WMCS), INSPEC Accession No. 17880625 DOI: 10.1109/WMCaS.2018.8400621 April 2018, incorporated herein by reference in its entirety).

The present disclosure utilizes equations (1) and (2) for calculating the capacitance and the resistance of multi-layers compositions inside a horizontal pipe especially for composition that occupy distinct layers. Equation (1) is verified against the theoretical development of an empty pipe, and against the more computationally involved Finite Difference (FD) method and experimental measurements.

Figure 1F:
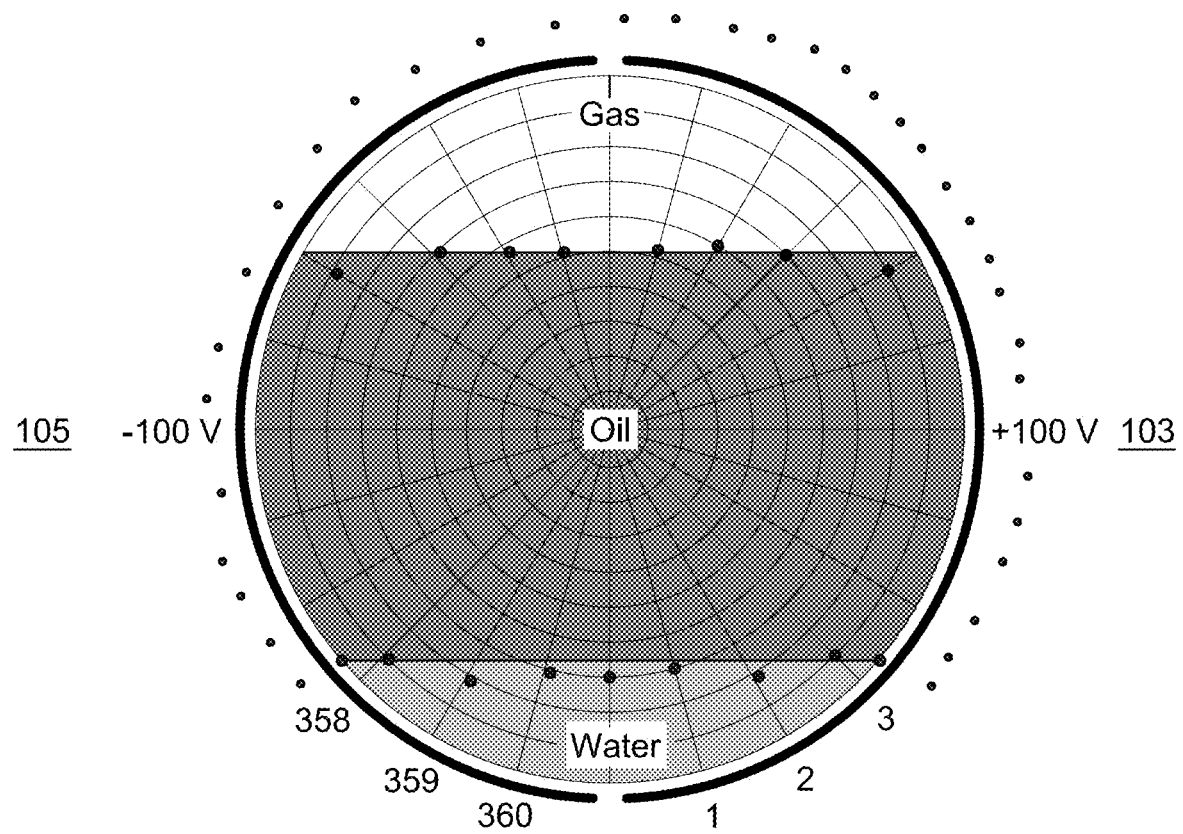
FIG. 1F illustrates the application of voltage to the conductive terminals in the experimental arrangement, according to certain embodiments.

FIGS. 1D, 1E and 1F demonstrate an experimental apparatus used to verify equation (1). A Plexiglas tube of 8.8 cm internal diameter with Plexiglas thickness of 0.5 cm was prepared. The pipe is placed horizontally. Two conducting sheets of length 25 cm were affixed to the internal surface of the Plexiglas tube separated at the top and bottom by 1 mm. The 1 mm separation in the bottom was filled with sand glue (as an insulator) so that when saline water partially fills the pipe, the conducting sheets do not short circuit. The two sheets have external terminals 103, 105 where an electrical signal was applied. The voltage applied at terminal 103 was 100 V and that applied at terminal 105 was −100 V.

Firstly, the capacitance of the empty pipe was measured. This was compared to the result obtained by equations (1) and (2). Secondly, a Finite Difference numerical algorithm was established and the capacitance of the empty pipe was calculated numerically by solving Laplace's equation as detailed by Iqbal. Additionally, the theoretical solution to solving for the capacitance of the empty pipe was formulated. The comparative results are presented in Table 4, which shows very close agreement between the calculation using equation 1 and the theoretical calculation, the finite difference calculation and the experimental results. Thus, equations (1) and (2) verify that the capacitance of the empty pipe can be determined by measuring the resistance in the experimental arrangement.

TABLE 4

Capacitance per unit length of empty circular pipe

| Theoretical | Finite Difference | Experimental (Iqbal) | Equation (1) |
|---|---|---|---|
| 117.29 pF/m | 116.41 pF/m | 117.08 pF/m | 117.69 pF/m |

Next, various volumes of saline water were fed into the pipe and the resistance Rp and capacitance Cp were measured across the two terminals described earlier. Cp is the sum of the capacitance of the water Cw plus the Cg of the gas plus Co of the oil. The Rp is the resistance of the water only which is related to Cw by equation (2). Equation is a fundamental equation in the electromagnetic field theory, (See M. N. Sadiku, "Elements of electromagnetics", Sixth edition, chapter 6, Oxford university press, 2015), herein incorporated by reference in its entirety.

Finally, the procedure outlined above in the calculations of the volumetric flow of oil per unit time (correlative flow method) were followed and several experiments were conducted to register the average percentage errors in the results. Table 5 gives the errors reported in the literature obtained using other techniques compared with the present procedure. The present procedure achieved a comparable error ratio with other methods. More details on the procedure may be found in the references above and in M. S. Iqbal. (See also X. Chen and L. Chen, "Crude Oil/Natural gas/Water Three-Phase Flow meter", SPE, 63rd annual technical conference and exhibition of the Society of Petroleum Engineers, Houston, Tex., Oct. 2-5, 1988; M. R. Taherian, T. M. Habashy, "Microwave Device and Method for Measuring Multiphase Flow," U.S. Pat. No. 5,485,743, Date: Jan. 23, 1996; P. Spedding, G. Donnelly and E. Benard, "Three Phase Oil-Water and Gas horizontal co-current flow Part II. Hold up measurement and prediction," Asia Pacific Journal of Chemical Engineering, 2007-2, pp. 130-136, each incorporated herein by reference in its entirety).

TABLE 5

Comparison of % errors (Room Temperature)

| Source | Chen | Taherian | Spedding | Xu | Isaksen | Qu | Present Technique |
|---|---|---|---|---|---|---|---|
| % Error | 5 | 5 | 3.7 | >5 | 30 | 8 | 6.3 |

Measurements were made using a setup of a closed pipe system with two pumps to control the flow of oil and brine and one pipe section internally covered with the electrodes as shown in FIG. 5A. FIG. 1E shows a Plexiglas pipeline section with integrated capacitors to measure the flow-rate. In a non-limiting example, Cp and Rp measurements were taken using a Keysight 2 MHz Precision LCR meter model E4980A (https://www.keysight.com/en/pd-715495-pn-E4980A/precision-lcr-meter-20-hz-to-2-mhz?cc=US&lc=eng). The measurements were performed at 10 kHz and repeated at 100 kHz and 1 MHz with almost identical results. The flow rate was 18.75 cm/s.

For an unknown three-phase stratified flow, the measured pipeline resistance ($R_T \cong R_W$) is superimposed in FIG. 2A. The measured $R_W$ is compared with the predicted resistance curve to identify phase angle $\beta_3$ related to the water level of the three-phase pipeline. The measured resistance ($\cong R_W$) with a known water level ($\beta_3$) is then substituted into $$R = \frac{\varepsilon_0 \varepsilon_r}{C\sigma}$$

to calculate the predicted capacitances ($C_W$) contributed by the electrode sections submerged within that water layer. The calculation of $C_W$ versus $\beta_3$ values are plotted in FIG. 2B. To validate these results, a separate measurement is performed by partially filling the semi-cylindrical capacitor with a water level equivalent to the three-phase mixture and recording the related capacitances. FIG. 2B superimposes the measured and calculated $C_W$ values, where minor discrepancies are mainly due to human error in determining the phase angle and differences in actual and predicted properties of water. Now, the LCR meter is used to measure the total capacitance ($C_T$) of the three-phase mixture. Since $C_T = C_G + C_O + C_W$ and $C_W$ values are known, the combined capacitances for gas ($C_G$) and oil ($C_O$) layers can be determined. FIG. 2C plots the calculated combined-capacitances ($C_C$) for known level ($\beta_3$) of the water layers. Thus, the phase angle ($\beta_1$) related to the gas contents of the pipeline with known values of $\beta_3$ and $C_C$ is determined from FIG. 2D. Note that the combined capacitances curves of FIG. 2C demonstrate negative slopes. This means that for a fixed water layer (or $\beta_3$), combined capacitance linearly decreases with increasing gas layer (or reducing $\beta_1$). This result indicates that increasing the gas layer (with lowest $\varepsilon_r$) decreases the effective dielectric constant of the combined gas-oil layer, resulting in a decrease in the combined capacitance. With known phase angles $\beta_3$ and $\beta_1$, oil contents of the pipeline are can then be easily calculated. In one of the experiments, the measurement apparatus of FIG. 1E and FIG. 5A is manipulated to establish a three-phase stratified flow with known phase-fractions of 2 mm, 24 mm and 6 mm thickness for water, oil and gas layers, respectively. This yields the cross-sectional area occupied by the oil contents ($CA_{oil}$) to be 6.789 cm$^2$. Then the above equations are used to determine the phase-fractions for comparison purposes. The process starts with measuring $C_T$=2.32 nF and $R_T$=2.86KΩ and using the equations above to calculate $\beta_3$=62, $C_W$=2.24 nF, $C_C$=80 pF, $\beta_1$=38° and $CA_{oil}$=6.584 cm$^2$. Note that this results in a percent error of approximately 6%. To verify the flow-rate calculation, the flow-rate-meter of FIG. 5A is used to establish a known flow-rate of 63.1 cm$^3$/sec for given layer thickness of water=2 mm, oil=15 mm and gas=15 mm. The methods of the present disclosure are then used to determine the flow-rate for error estimation purposes. This process starts by measuring the capacitances and resistances of the two cylindrical capacitors, and using cross-correlation to identify the time delay ($T_0$) of 3.2 s. This results in a predicted flow rate of 65.4 cm$^3$/s, with a percent-error of 3%. Table 3 compares the average error margin of the present disclosure with errors reported in the literature. Note that low error rate reported in the literature involved a more complicated measurement system.

TABLE 3

Comparison of percent-errors (25° C.)

|  | Ref. [1] | Ref. [2] | Ref. [3] | Ref. [4] | Ref. [5] | Ref. [6] | Experimental results |
|---|---|---|---|---|---|---|---|
| Reported Error | 5% | 5% | 3.7% | >5% | 30% | 8% | 6.3% |

(See [1] X. Chen and L. Chen, "Crude Oil/Natural gas/Water Three-Phase Flow meter," SPE, 63rd annual technical conference and exhibition of the Society of Petroleum Engineers, Houston, Tex., 2-5 Oct. 1988.[2]M. R. Taherian, T. M. Habashy, "Microwave Device and Method for Measuring Multiphase Flow," U.S. Pat. No. 5,485,743, Date: 23 Jan. 1996. [3] P. Spedding, G. Donnelly and E. Benard, "Three Phase Oil-Water and Gas horizontal co-current flow Part II. Hold up measurement and prediction," Asia Pacific Journal of Chemical Engineering, Vol. 2, No. 2, pp. 130-136, March 2007. [4] L. Al-Hadhrami, S. Shaahid, L. Tund and A. Al-Sarkhi, "Experimental study on the flow regimes and pressure gradients of air-oil-water three-phase flow in horizontal pipes," Scientific World Journal, vol. 2014, January 2014. [5] Michel Bérard and Ibrahim Babelli, "System and Method for Measuring Flow in a Pipeline", U.S. Pat. No. 7,726,185, Date: 1 Jun. 2010. [6] O. Isaksen, "Three Phase Pipe Flow Imaging Using a Capacitance Tomography System," IEEE Colloquium on Advances in Sensors for Fluid Flow Measurements, pp 11/1-11/6, 18 Apr. 1996, each herein incorporated by reference in its entirety).

The present disclosure presents a novel technique for estimating and determining the amounts of water and oil in a three-phase flow using simple electrical measurements. The results are comparable with relatively complicated methods reported in the literature.

Figure 7:
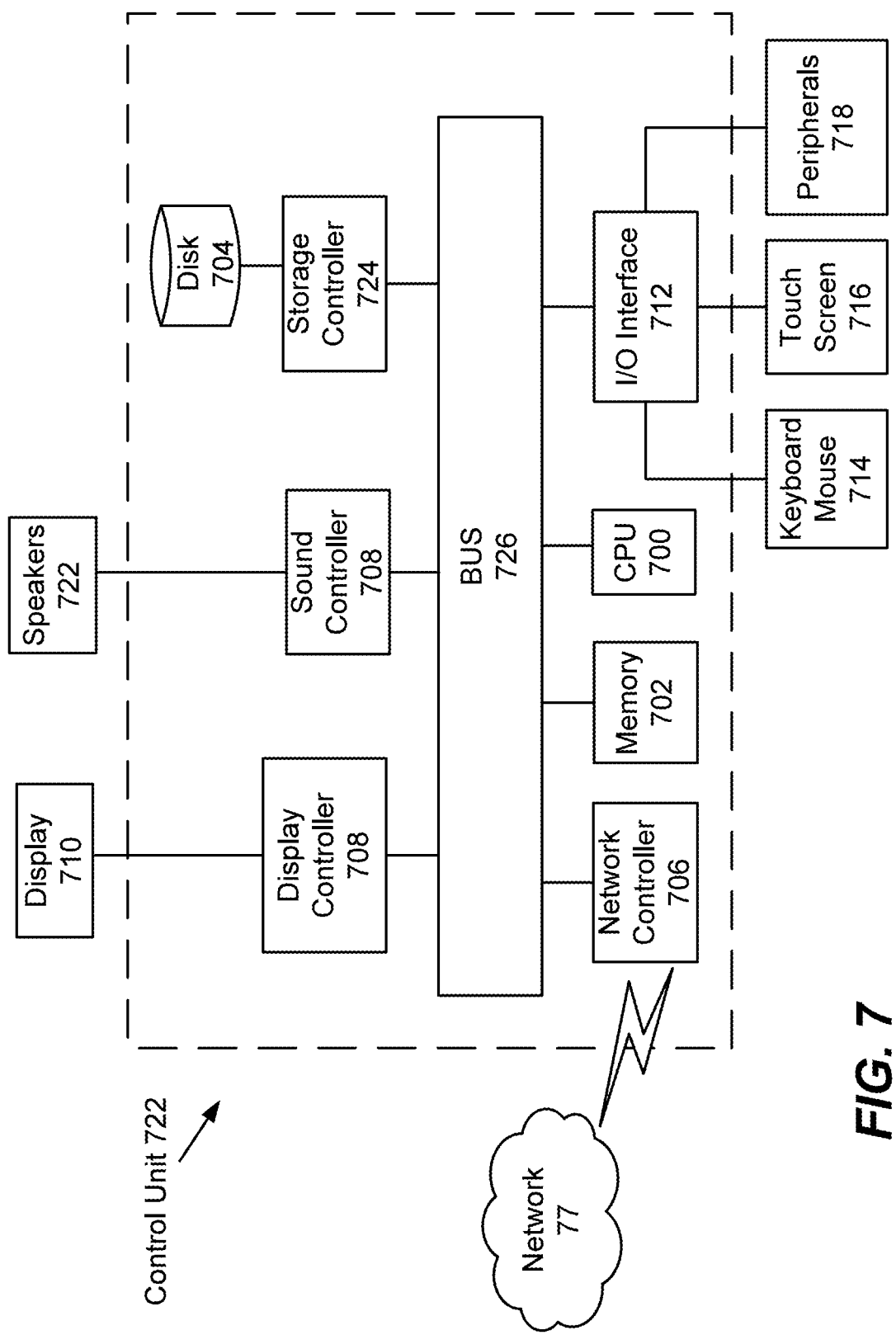
FIG. 7 is an exemplary illustration of computing hardware used in the control units of the exemplary embodiments.

Next, a hardware description of the control unit according to exemplary embodiments is described with reference to FIG. 7. In FIG. 7, the controller described is representative of the control unit 350 in which the controller is computing device which includes a CPU 700 which performs the processes described above/below. The process data and instructions may be stored in memory 702. These processes and instructions may also be stored on a storage medium disk 704 such as a hard drive (HDD) or portable storage medium or may be stored remotely.

Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device communicates, such as a server or computer.

Further, the claimed advancements may be provided as a utility application, background daemon, or component of an operating system, or combination thereof, executing in conjunction with CPU 700 and an operating system such as Microsoft Windows 7, UNI7, Solaris, LINU7, Apple MAC-OS and other systems known to those skilled in the art.

The hardware elements in order to achieve the computing device may be realized by various circuitry elements, known to those skilled in the art. For example, CPU 700 may be a Xenon or Core processor from Intel of America or an Opteron processor from AMD of America, or may be other processor types that would be recognized by one of ordinary skill in the art. Alternatively, the CPU 700 may be implemented on an FPGA, ASIC, PLD or using discrete logic circuits, as one of ordinary skill in the art would recognize. Further, CPU 700 may be implemented as multiple processors cooperatively working in parallel to perform the instructions of the inventive processes described above.

The computing device in FIG. 7 also includes a network controller 706, such as an Intel Ethernet PRO network interface card from Intel Corporation of America, for interfacing with network 77. As can be appreciated, the network 77 can be a public network, such as the Internet, or a private network such as an LAN or WAN network, or any combination thereof and can also include PSTN or ISDN subnetworks. The network 77 can also be wired, such as an Ethernet network, or can be wireless such as a cellular network including EDGE, 3G and 4G wireless cellular systems. The wireless network can also be WiFi, Bluetooth, or any other wireless form of communication that is known.

The computing device further includes a display controller 708, such as a NVIDIA GeForce GT7 or Quadro graphics adaptor from NVIDIA Corporation of America for interfacing with display 710, such as a Hewlett Packard HPL2445w LCD monitor. A general purpose I/O interface 712 interfaces with a keyboard and/or mouse 714 as well as a touch screen panel 716 on or separate from display 710. General purpose I/O interface also connects to a variety of peripherals 718 including printers and scanners, such as an OfficeJet or DeskJet from Hewlett Packard.

A sound controller 720 is also provided in the computing device such as Sound Blaster 7-Fi Titanium from Creative, to interface with speakers/microphone 722 thereby providing sounds and/or music.

The general purpose storage controller 724 connects the storage medium disk 704 with communication bus 726, which may be an ISA, EISA, VESA, PCI, or similar, for interconnecting all of the components of the computing device. A description of the general features and functionality of the display 710, keyboard and/or mouse 714, as well as the display controller 708, storage controller 724, network controller 706, sound controller 720, and general purpose I/O interface 712 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset, as shown on FIG. 8.

Figure 8:
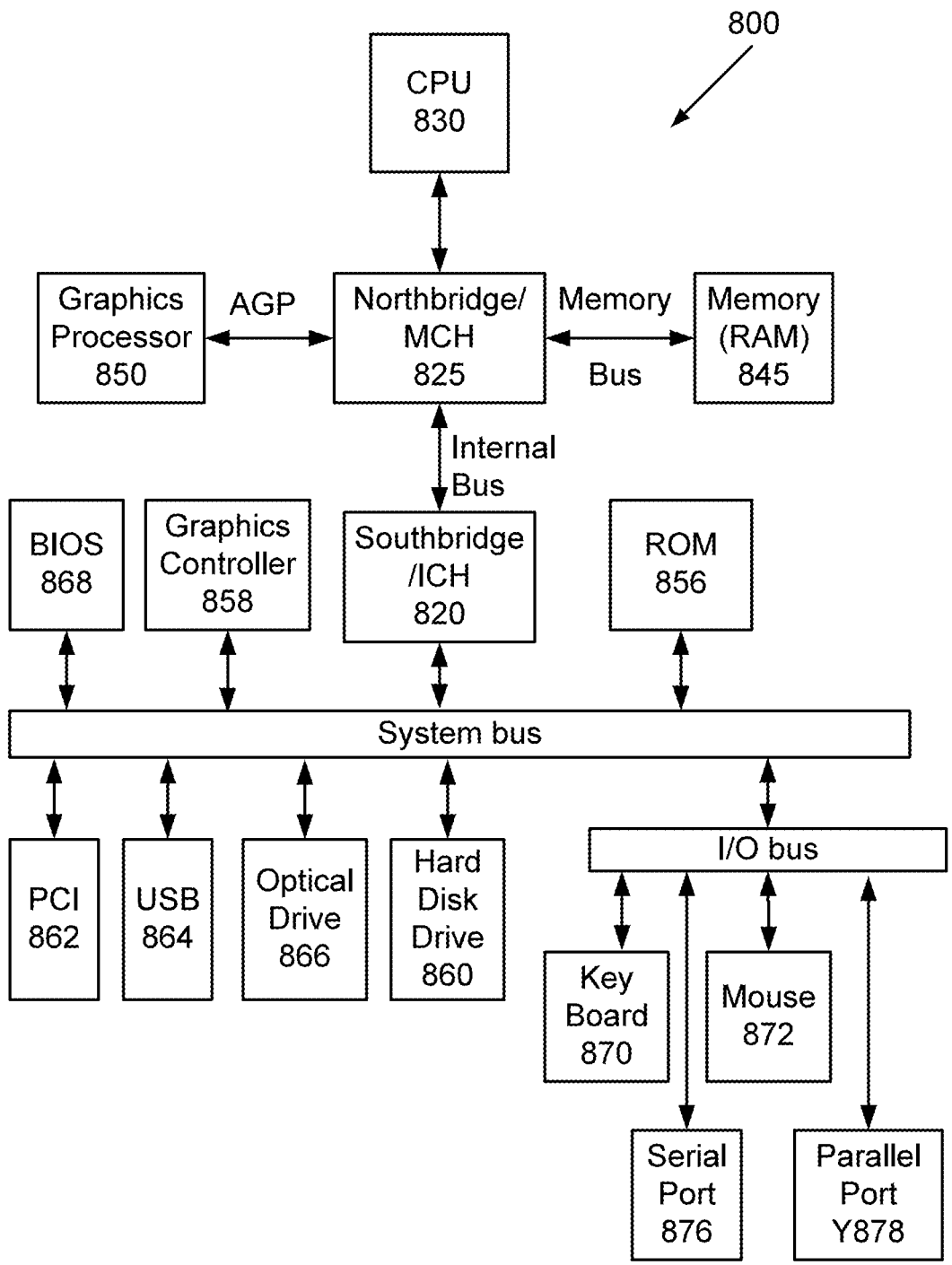
FIG. 8 is an exemplary schematic diagram of a data processing system used within the control units, according to certain embodiments.

FIG. 8 shows a schematic diagram of a data processing system, according to certain embodiments, for performing the functions of the exemplary embodiments. The data processing system is an example of a computer in which code or instructions implementing the processes of the illustrative embodiments may be located.

In FIG. 8, data processing system 800 employs a hub architecture including a north bridge and memory controller hub (NB/MCH) 825 and a south bridge and input/output (I/O) controller hub (SB/ICH) 820. The central processing unit (CPU) 830 is connected to NB/MCH 825. The NB/MCH 825 also connects to the memory 845 via a memory bus, and connects to the graphics processor 850 via an accelerated graphics port (AGP). The NB/MCH 825 also connects to the SB/ICH 820 via an internal bus (e.g., a unified media interface or a direct media interface). The CPU Processing unit 830 may contain one or more processors and even may be implemented using one or more heterogeneous processor systems.

Figure 9:
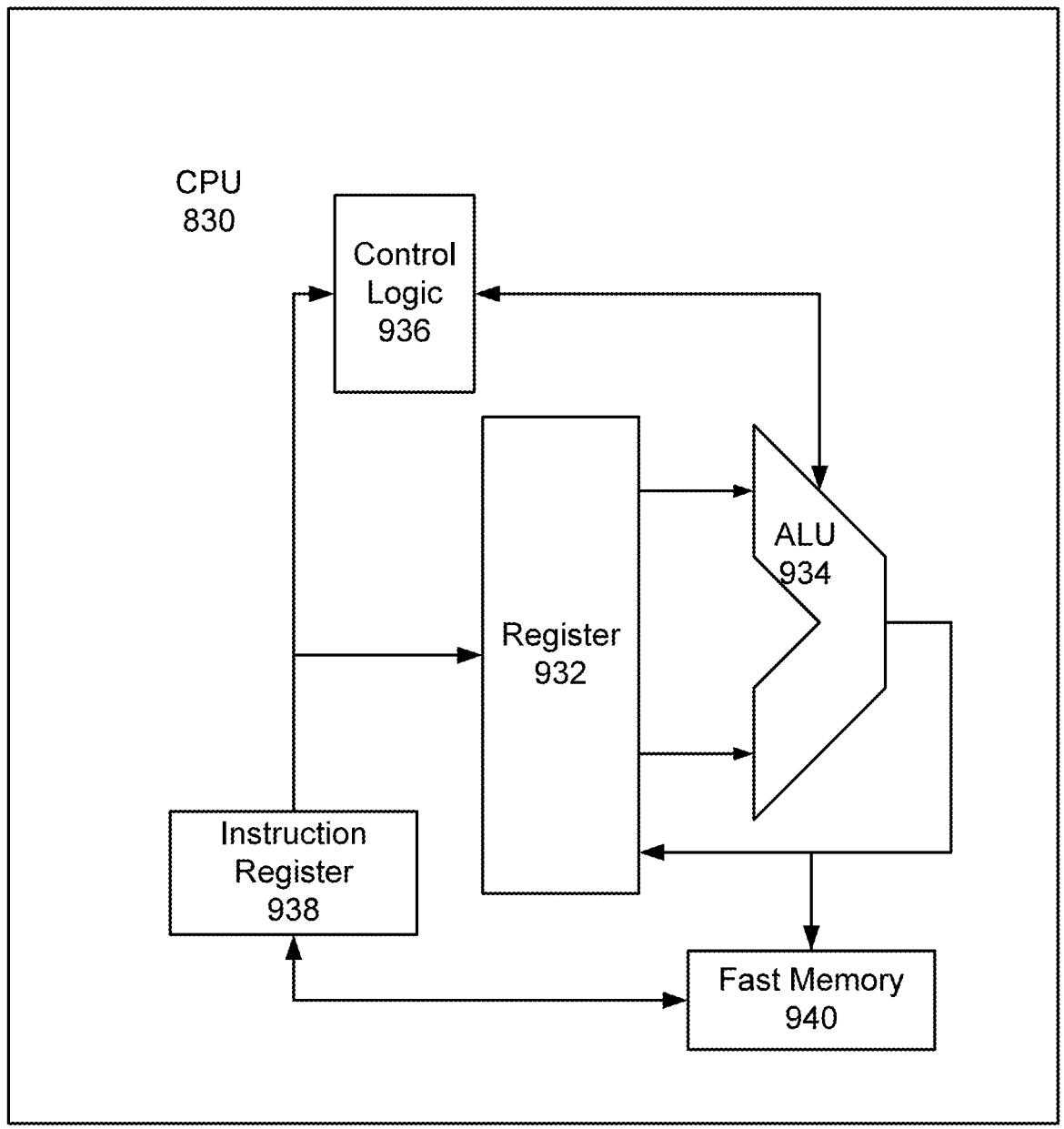
FIG. 9 is an exemplary schematic diagram of a CPU used in the control units according to certain embodiments.

For example, FIG. 9 shows one implementation of CPU 830. In one implementation, the instruction register 938 retrieves instructions from the fast memory 940. At least part of these instructions are fetched from the instruction register 938 by the control logic 936 and interpreted according to the instruction set architecture of the CPU 830. Part of the instructions can also be directed to the register 932. In one implementation the instructions are decoded according to a hardwired method, and in another implementation the instructions are decoded according a microprogram that translates instructions into sets of CPU configuration signals that are applied sequentially over multiple clock pulses. After fetching and decoding the instructions, the instructions are executed using the arithmetic logic unit (ALU) 934 that loads values from the register 932 and performs logical and mathematical operations on the loaded values according to the instructions. The results from these operations can be feedback into the register and/or stored in the fast memory 940. According to certain implementations, the instruction set architecture of the CPU 830 can use a reduced instruction set architecture, a complex instruction set architecture, a vector processor architecture, a very large instruction word architecture. Furthermore, the CPU 830 can be based on the Von Neuman model or the Harvard model. The CPU 830 can be a digital signal processor, an FPGA, an ASIC, a PLA, a PLD, or a CPLD. Further, the CPU 830 can be an x86 processor by Intel or by AMD; an ARM processor, a Power architecture processor by, e.g., IBM; a SPARC architecture processor by Sun Microsystems or by Oracle; or other known CPU architecture.

Referring again to FIG. 8, the data processing system 800 can include that the SB/ICH 820 is coupled through a system bus to an I/O Bus, a read only memory (ROM) 856, universal serial bus (USB) port 864, a flash binary input/output system (BIOS) 868, and a graphics controller 858. PCI/PCIe devices can also be coupled to SB/ICH 888 through a PCI bus 862.

The PCI devices may include, for example, Ethernet adapters, add-in cards, and PC cards for notebook computers. The Hard disk drive 860 and CD-ROM 866 can use, for example, an integrated drive electronics (IDE) or serial advanced technology attachment (SATA) interface. In one implementation the I/O bus can include a super I/O (SIO) device.

Further, the hard disk drive (HDD) 860 and optical drive 866 can also be coupled to the SB/ICH 820 through a system bus. In one implementation, a keyboard 870, a mouse 872, a parallel port 878, and a serial port 876 can be connected to the system bus through the I/O bus. Other peripherals and devices that can be connected to the SB/ICH 820 using a mass storage controller such as SATA or PATA, an Ethernet port, an ISA bus, a LPC bridge, SMBus, a DMA controller, and an Audio Codec.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry, or based on the requirements of the intended back-up load to be powered.

Figure 10:
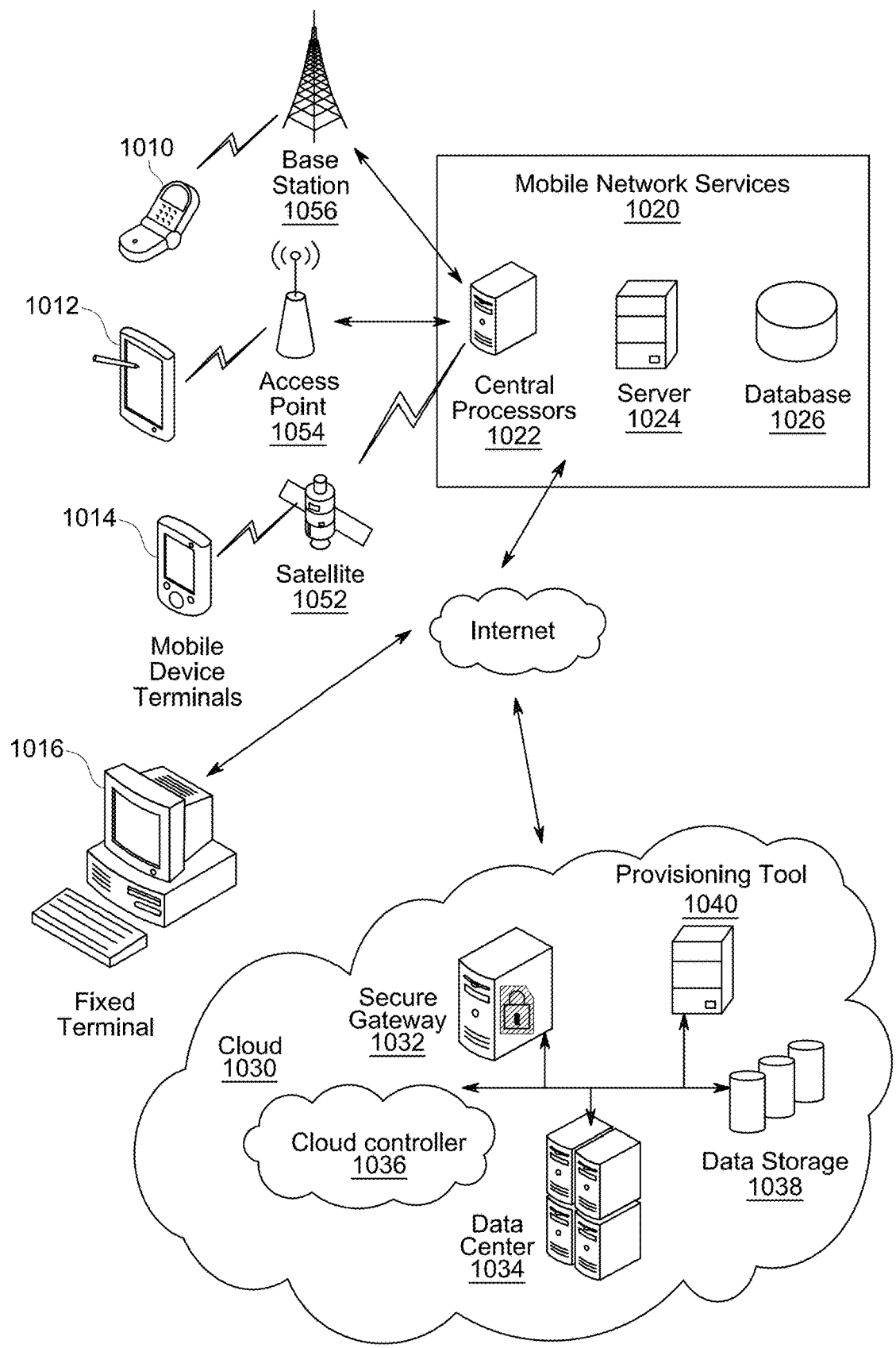
FIG. 10 is an illustration of a non-limiting example of distributed components which may share processing with the control units, according to certain embodiments.

The functions and features described herein may also be executed by various distributed components of a system. For example, one or more processors may execute these system functions, wherein the processors are distributed across multiple components communicating in a network. The distributed components may include one or more client and server machines, which may share processing, as shown on FIG. 10, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely either in real-time or as a batch process. Additionally, some implementations may be performed on modules or hardware not identical to those described. Accordingly, other implementations are within the scope that may be claimed.

The above-described hardware description is a non-limiting example of corresponding structure for performing the functionality described herein.

In conclusion, a simple inclined capacitive plate apparatus is proposed to determine the phase-fractions and the flow-rate of a three-phase pipeline with wavy-stratified flow. A method relates the measured capacitances and resistances of the mixture with phase angles of water and gas layers to determine the volume ratio. A capacitor with a set of semi-cylindrical electrodes, mounted on the inner or outer surface of the pipe, is used for this purpose. To find the flow-rate, a set of capacitors with known separation distance is used to measure the time-delay required for a surge in the fluid flow to pass through the capacitors. Standard cross-correlation of measured capacitances is used for this purpose. The predicted phase-fractions and flow-rate are experimentally verified and an error rate of 6.3% is observed.

Obviously, numerous modifications and variations of the present invention are possible in light of the above teachings. It is therefore to be understood that within the scope of the appended claims, the invention may be practiced otherwise than as specifically 1 to described herein.

Various alternatives and modifications can be devised by those skilled in the art without departing from the disclosure. Accordingly, the present disclosure is intended to embrace all such alternatives, modifications and variances. Additionally, while several embodiments of the present disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. And, those skilled in the art will envision other modifications within the scope and spirit of the claims appended hereto. Other elements, steps, methods and techniques that are insubstantially different from those described above and/or in the appended claims are also intended to be within the scope of the disclosure.

The embodiments shown in the drawings are presented only to demonstrate certain examples of the disclosure. And, the drawings described are only illustrative and are non-limiting. In the drawings, for illustrative purposes, the size of some of the elements may be exaggerated and not drawn to a particular scale. Additionally, elements shown within the drawings that have the same numbers may be identical elements or may be similar elements, depending on the context.

Where the term "comprising" is used in the present description and claims, it does not exclude other elements or steps. Where an indefinite or definite article is used when referring to a singular noun, e.g. "a" "an" or "the", this includes a plural of that noun unless something otherwise is specifically stated. Hence, the term "comprising" should not be interpreted as being restricted to the items listed thereafter; it does not exclude other elements or steps, and so the scope of the expression "a device comprising items A and B" should not be limited to devices consisting only of components A and B. This expression signifies that, with respect to the present disclosure, the only relevant components of the device are A and B.

Furthermore, the terms "first", "second", "third" and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

While preferred embodiments have been shown and described, various modifications and substitutions may be made thereto without departing from the spirit and scope of the invention. Accordingly it is to be understood that the present invention has been described by way of illustrations and not limitations.

The invention claimed is:

1. An apparatus for measuring water, oil and gas volumes within a cylindrical horizontal pipeline and the velocity of the oil flowing in the pipeline, wherein the pipeline has a circular cross-sectional area of radius (Rad), and an axial length (Z), the apparatus comprising:

the pipeline including a plurality of pipe sections, wherein at least one pipe section has an internal structure including a first semi-cylindrical conducting sheet covering a portion of the internal surface of the pipe section and a second semi-cylindrical conducting sheet covering an opposing portion of the internal surface of the pipe section, wherein each semi-cylindrical sheet has radius (Rad) and axial length $z_0$, wherein the at least one pipe section is installed a first location within the pipeline, wherein a gap ($2\delta$) exists between an edge of the first semi-cylindrical conducting sheet and a corresponding edge of the second semi-cylindrical conducting sheet;

a conductive terminal installed along the central axial line of the first semi-cylindrical conducting sheet and a corresponding conductive terminal installed at the central axial line of the second semi-cylindrical conducting sheet, wherein each conductive terminal is placed on the external surface of the pipe section and protrudes through the pipe section to electrically contact a respective semi-cylindrical sheet; and a control unit comprising:
  a power supply to apply a positive DC voltage at the first terminal and a negative DC voltage at the second terminal;
  a switch connected between the power supply and the first terminal;
  a controller having circuitry configured to control the switch;
  measuring circuitry connected to the conductive terminals to measure the capacitance and resistance between the terminals, the resistance of the semi-cylindrical sheets; and
  processing circuitry configured determine the respective volumes of water, oil and gas in the pipe sections based on the capacitance and resistance measurements and to calculate the velocity of the oil flowing in the pipeline, and wherein the processing circuitry is further configured to calculate the capacitance measurement of the water based on the measured resistance and the equations:

$$C = \frac{\varepsilon_0 \varepsilon_r}{2\phi_0} \ln\left(\frac{b}{a}\right) \; F/m \text{ and } R = \frac{\varepsilon_0 \varepsilon_r}{C\sigma},$$

wherein $\sigma$ is the conductivity of the brine or water; $\varepsilon_0$ is the dielectric constant of water; and $\varepsilon_r$ is the relative dielectric constant of the brine, wherein $\delta$ is the angle subtended by a sector from the center of the pipe section to the edge of the gap; N is the number of chords subtended by an angle $2\delta$, wherein N is an even number and an integer; $\beta 1$ is the angle from the center of the pipe section to the top of the oil volume, $\beta 2$ is the angle from the center of the pipe section to the top of the water volume and $a_n = \rho_0 * \{\cos(\delta)\cot(\beta_{2n}) - \sin(\delta)\}$ $b_n = \rho_0 * \{\cos(\delta)\cot(\beta_{2n}) + \sin(\delta)\}$ $\beta_{2n} = (2n+1)\delta$ radians, with n=0, 1, 2 ... N, $$N = \left(\frac{90°}{2\delta}\right) - 1$$

and $\phi_n = \beta_{2n}$ radians.

2. The apparatus of claim 1, wherein the processing circuitry is further configured to calculate the total resistance and the total capacitance of the semi-cylindrical sheets based on the following equations:

$$R_T = \sum_1^N \left(\frac{1}{\sigma}\right) 2\phi_n / \ln(b_n/a_n) \; \Omega/m \text{ and}$$

$$C_T = \sum_{n=0}^N \left(\frac{\varepsilon_0 \varepsilon_r}{2\phi_n} \ln\left(\frac{b_n}{a_n}\right)\right) \quad F/m.$$

3. The apparatus of claim 1, wherein the water content has a height (hw) measured along the vertical radius of the cross section of the pipe section, wherein the oil content has a height (ho) measured along the vertical radius of the cross section of the pipe section, wherein the gas has a height (hg) measured along the vertical radius of the cross section of the pipe section, wherein 2Rad=hw+ho+hg, and wherein the processing circuitry is further configured to calculate the respective heights of the oil, water and gas within the pipe section.

4. The apparatus of claim 1, further comprising:
a second pipe section having a second internal structure installed at a second location within the pipeline, the second internal structure separated by a distance (d) from the first internal structure,
wherein second capacitance measurements are made at the second location at a time ($\tau_0$), wherein ($\tau_0$) is the time elapsed between a capacitance measurement at the first location and a capacitance measurement at the second location, and
wherein the processing circuitry is configured to calculate the velocity of the oil flowing in the pipeline based on the equation velocity=d/$\tau_0$ and the capacitance measurements of the first pipe section and the second capacitance measurements of the second pipe section.

5. The apparatus of claim 4, wherein the processing circuitry is configured to calculate the volume of oil flowing per unit time, based on:

$$\text{Volume of } \frac{\text{oil}}{\text{time}} = (\pi * \text{Rad}^2 - V_g - V_w) * \text{velocity},$$

wherein Rad is the pipe radius and Vg, and Vw are the gas and water volumes respectively, given by:

$V_g = \beta 1 \times \text{Rad}^2 - \text{Rad}^2 \times \cos(\beta 1) \times \sin(\beta 1)$ $V_b = \beta 3 \times \text{Rad}^2 - \text{Rad}^2 \times \cos(\beta 3) \times \sin(\beta 3)$ 6. The apparatus of claim 1, further comprising:
wherein the control unit is located within a recessed compartment on the external surface of the pipe section;
wherein wiring connects the conductive terminals to the controller;
wherein a cover protects the control unit, wiring and conductive terminals, wherein the cover is hermetically sealed to the surface of the pipe section.

7. The apparatus of claim 5, wherein the control unit further comprises a communications unit having communications circuitry capable of transmitting the measurements of the volumes of water, oil and gas in the pipe section and the velocity of the oil flowing in the pipeline between the first and second sections to a remote control center using wired or wireless communication.

8. The apparatus of claim 5, wherein the control unit further comprises a communications unit having communications circuitry capable of transmitting the measurements of the volumes of water, oil and gas in the pipe section and the velocity of the oil flowing in the pipeline between the first and second sections to a remote computing station using wires embedded within the plurality of pipeline sections.

9. The apparatus of claim 5, wherein the control unit further comprises a communications unit having communications circuitry capable of wirelessly transmitting the measurements of the volumes of water, oil and gas in the pipe section and the velocity of the oil flowing in the pipeline between the first and second sections to a remote terminal unit (RTU), wherein the remote terminal unit transmits the measurements to a remote control center by wireless communication, wherein the wireless communication is at least one of microwave communications (WiMAX), 3G, 4G, LTE, Wifi, LAN, WAN and satellite communications.

10. A method for measuring water, oil and gas volumes within a cylindrical horizontal pipeline and the velocity of the oil flowing in the pipeline, wherein the pipeline has a circular cross-sectional area of radius (Rad), and an axial length (Z), the method comprising:
installing, within the pipeline having a plurality of pipe sections, at least one pipe section having an internal structure including a first semi-cylindrical conducting sheet covering a portion of the internal surface of the pipe section and a second semi-cylindrical conducting sheet covering an opposing portion of the internal surface of the section of the pipe section, wherein each semi-cylindrical sheet has radius (Rad) and axial length $z_0$, so that a gap ($2\delta$) exists between an edge of the first semi-cylindrical conducting sheet and a corresponding edge of the second semi-cylindrical conducting sheet, installing a first conductive terminal along the central axial line of the first semi-cylindrical conducting sheet and a second conductive terminal at the central axial line of the second semi-cylindrical conducting sheet so that each conductive terminal is located on the external surface of the pipe section and protrudes through the pipe section to electrically contact a respective semi-cylindrical sheet;

connecting the conductive terminals to a control unit including a controller having circuitry configured for applying a positive DC voltage at the first terminal and a negative DC voltage at the second terminal and for measuring the resistance and capacitance at the conductive terminals, and the resistance of the semi-cylindrical sheets; the control unit further having processing circuitry for determining the respective volumes of water, oil and gas in the pipe section and calculating the velocity of the oil flowing in the pipeline, and wherein the processing circuitry is further configured to calculate the capacitance measurement of the water based on the measured resistance and the equations:

$$C = \frac{\varepsilon_0 \varepsilon_r}{2\phi_0} \ln\left(\frac{b}{a}\right) \, F/m \text{ and } R = \frac{\varepsilon_0 \varepsilon_r}{C\sigma},$$

wherein $\sigma$ is the conductivity of the brine or water; $\varepsilon_0$ is the dielectric constant of water; and $\varepsilon_r$ is the relative dielectric constant of the brine, wherein $\delta$ is the angle subtended by a sector from the center of the pipe section to the edge of the gap; N is the number of chords subtended by an angle $2\delta$, wherein N is an even number and an integer; $\beta1$ is the angle from the center of the pipe section to the top of the oil volume, $\beta2$ is the angle from the center of the pipe section to the top of the water volume and $a_n = \rho_0 * \{\text{Cos}(\delta)\text{cot}(\beta_{2n}) - \text{Sin}(\delta)\}$ $b_n = \rho_0 * \{\text{Cos}(\delta)\text{cot}(\beta_{2n}) + \text{Sin}(\delta)\}$ $\beta_{2n} = (2n+1)\delta \text{ radians},$ with n=0, 1, 2 . . . N, $$N = \left(\frac{90°}{2\delta}\right) - 1$$

and $\phi_n = \beta_{2n}$ radians.

11. The method of claim 1, wherein the processing circuitry is configured to calculate the total resistance and the total capacitance of the semi-cylindrical sheets based on the following equations:

$$R_T = \sum_{1}^{N} \left(\frac{1}{\sigma}\right) 2\phi_n / \ln(b_n/a_n) \quad \Omega/m \text{ and}$$

$$C_T = \sum_{n=0}^{N} \left(\frac{\varepsilon_0 \varepsilon_r}{2\phi_n} \ln\left(\frac{b_n}{a_n}\right)\right) \quad \frac{F}{m}.$$

12. The method of claim 10, further comprising determining, by the processing circuitry, the capacitance of the water, the water including brine, based on the equation:

$C_w = \varepsilon_o \varepsilon_{rb}/(\sigma R) \text{Farad}/m$ and defining the volume of water as having a height (hw) measured along the vertical radius of the cross section of the pipe section, the oil content as having a height (ho) measured along the vertical radius of the cross section of the pipe section, the gas as having a height (hg) measured along the vertical radius of the cross section of the pipe section, wherein 2Rad=hw+ho+hg, and calculating, by the processing circuitry, the respective heights of the water, oil and gas within the pipeline.

13. The method of claim 10, further comprising:
installing a second pipe section having a second internal structure at a second location within the pipeline, the second internal structure separated by a distance (d) from the first internal structure, measuring a second capacitance and a second resistance at the second location at a time ($\tau_O$), wherein ($\tau_O$) is the time elapsed between a capacitance measurement at the first location and a capacitance measurement at the second location, and calculating, by the processing circuitry, the velocity of the oil flowing in the pipeline based on the equation velocity=$\tau_O$ and the capacitance and resistance measurements of the first pipe section and the second capacitance and second resistance measurements of the second pipe section.

14. The method of claim 13, further comprising calculating, by the processing circuitry, the volume of oil flowing per unit time, based on:

$$\text{Volume of } \frac{\text{oil}}{\text{time}} = (\pi * \text{Rad}^2 - V_g - V_w) * \text{velocity},$$

wherein Rad is the pipe radius and Vg, and Vw are the gas and water volumes respectively, given by:

$V_g = \beta1 \times \text{Rad}^2 - \text{Rad}^2 \times \cos(\beta1) \times \sin(\beta1)$ $V_b = \beta3 \times \text{Rad}^2 - \text{Rad}^2 \times \cos(\beta3) \times \sin(\beta3)$ 15. The method of claim 14, further comprising transmitting, by communications circuitry in the control unit, the measurements of the volumes of water, oil and gas in the pipe section and the velocity of the oil flowing in the pipeline between the first and second sections to a remote control center using at least one of wired communication, wireless communication and wires embedded within the plurality of pipeline sections.

16. The method of claim 15, further comprising transmitting, by communications circuitry in the control unit, the measurements of the volumes of water, oil and gas in the pipe section and the velocity of the oil flowing in the pipeline between the first and second sections to a remote terminal unit (RTU), wherein the remote terminal unit transmits the measurements to a remote control center by wireless communication, wherein the wireless communication is at least one of microwave communications (WiMAX), 3G, 4G, LTE, Wifi, LAN, WAN and satellite communications.

17. A non-transitory computer readable medium having instructions stored therein that, when executed by one or more processors, cause the one or more processors to perform a method for measuring water, oil and gas volumes within a cylindrical horizontal pipeline and the velocity of the oil flowing in the pipeline, wherein the pipeline has a circular cross-sectional area of radius (Rad) and an axial length (Z), the pipeline having a plurality of pipe sections, at least one pipe section having an internal structure including a first semi-cylindrical conducting sheet covering a portion of the internal surface of the pipe section and a second semi-cylindrical conducting sheet covering an opposing portion of the internal surface of the section of the pipe section, wherein each semi-cylindrical sheet has radius (Rad) and axial length $z_0$, so that a gap ($2\delta$) exists between an edge of the first semi-cylindrical conducting sheet and a corresponding edge of the second semi-cylindrical conducting sheet, and a first conductive terminal installed along the central axial line of the first semi-cylindrical conducting sheet and a second conductive terminal installed at the central axial line of the second semi-cylindrical conducting sheet so that each conductive terminal is located on the external surface of the pipe section and protrudes through the pipe section to electrically contact a respective semi-cylindrical sheet; the non-transitory computer readable medium method comprising:

applying a positive DC voltage at the first terminal and a negative DC voltage at the second terminal, the conductive terminals connected to a control unit;

measuring, by a controller in the control unit and having circuitry configured for measuring, the resistance at the first and second terminals;

calculating, by processing circuitry in the control unit, the capacitance measurement of the water based on the measured resistance and the equations:

$$C = \frac{\varepsilon_0 \varepsilon_r}{2\phi_0} \ln\left(\frac{b}{a}\right) \ F/m \text{ and } R = \frac{\varepsilon_0 \varepsilon_r}{C\sigma},$$

wherein $\sigma$ is the conductivity of the brine or water; $\varepsilon_0$ is the dielectric constant of water; and $\varepsilon_r$ is the relative dielectric constant of the brine, wherein $\delta$ is the angle subtended by a sector from the center of the pipe section to the edge of the gap; N is the number of chords subtended by an angle $2\delta$, wherein N is an even number and an integer; $\beta1$ is the angle from the center of the pipe section to the top of the oil volume, $\beta2$ is the angle from the center of the pipe section to the top of the water volume and $a_n = \rho_0 * \{\cos(\delta)\cot(\beta_{2n}) - \sin(\delta)\}$ $b_n = \rho_0 * \{\cos(\delta)\cot(\beta_{2n}) + \sin(\delta)\}$ $\beta_{2n} = (2n+1)\delta$ radians, with n=0, 1, 2 . . . N, $$N = \left(\frac{90°}{2\delta}\right) - 1$$

and $\phi_n = \beta_{2n}$ radians;

calculating the total resistance and the total capacitance of the semi-cylindrical sheets based on the following equations:

$$R_T = \sum_{1}^{N}\left(\frac{1}{\sigma}\right) 2\phi_n / \ln(b_n/a_n) \quad \Omega/m \text{ and}$$

$$C_T = \sum_{n=0}^{N}\left(\frac{\varepsilon_0 \varepsilon_r}{2\phi_n}\ln\left(\frac{b_n}{a_n}\right)\right) \ F/m.$$

determining, the respective volumes of water, oil and gas in the pipe section and calculating the velocity of the oil flowing in the pipeline;

determining, by the processing circuitry, the capacitance of the water, the water including brine, based on the equation:

$Cw = \varepsilon_o \varepsilon_{rb}/(\sigma R)$ Farad/m defining, by the processing circuitry, the volume of water as having a height (hw) measured along the vertical radius of the cross section of the pipe section, the oil content as having a height (ho) measured along the vertical radius of the cross section of the pipe section, the gas as having a height (hg) measured along the vertical radius of the cross section of the pipe section, wherein 2Rad=hw+ho+hg, and calculating, by the processing circuitry, the respective heights of the water, oil and gas within the pipeline;

measuring at a time ($\tau0$), second capacitance and second resistance at a second pipe section having a second internal structure and located at a second location within the pipeline, the second internal structure separated by a distance (d) from the first internal structure, wherein ($\tau_0$) is the time elapsed between a capacitance measurement at the first location and a capacitance measurement at the second location, and calculating, by the processing circuitry, the velocity of the oil flowing in the pipeline based on the equation velocity=$\tau_0$, the capacitance and resistance measurements of the first pipe section and the second capacitance and second resistance measurements of the second pipe section;

calculating, by the processing circuitry, the volume of oil flowing per unit time, based on the equation:

$$\text{Volume of } \frac{\text{oil}}{\text{time}} = (\pi * \text{Rad}^2 - V_g - V_w) * \text{velocity},$$

wherein Rad is the pipe radius and Vg, and Vw are the gas and water volumes respectively, given by:

$V_g = \beta1 \times \text{Rad}^2 - \text{Rad}^2 \times \cos(\beta1) \times \sin(\beta1)$ $V_b = \beta3 \times \text{Rad}^2 - \text{Rad}^2 \times \cos(\beta3) \times \sin(\beta3)$ transmitting, by communications circuitry in the control unit, the measurements of the volumes of water, oil and gas in the pipe section and the velocity of the oil flowing in the pipeline between the first and second sections to a remote control center using wired or wireless communication.

* * * * *